(12) United States Patent
Hancock et al.

(10) Patent No.: US 11,553,955 B2
(45) Date of Patent: Jan. 17, 2023

(54) CABLE FOR CONVEYING RADIOFREQUENCY AND/OR MICROWAVE FREQUENCY ENERGY TO AN ELECTROSURGICAL INSTRUMENT

(71) Applicant: CREO MEDICAL LIMITED, Chepstow (GB)

(72) Inventors: Christopher Paul Hancock, Bath (GB); Malcolm White, Monmouthshire (GB); George Christian Ullrich, Gwynedd (GB); David Edward Webb, Gwynedd (GB); Louis Turner, Monmouthshire (GB); Steven Morris, Monmouthshire (GB)

(73) Assignee: CREO MEDICAL LIMITED, Chepstow (GB)

( * ) Notice: Subject to any disclaimer, the term of this patent is extended or adjusted under 35 U.S.C. 154(b) by 1432 days.

(21) Appl. No.: 15/518,207

(22) PCT Filed: Oct. 16, 2015

(86) PCT No.: PCT/EP2015/074047
§ 371 (c)(1),
(2) Date: Apr. 10, 2017

(87) PCT Pub. No.: WO2016/059228
PCT Pub. Date: Apr. 21, 2016

(65) Prior Publication Data
US 2017/0303986 A1     Oct. 26, 2017

(30) Foreign Application Priority Data

Oct. 17, 2014 (GB) ...................... 1418486

(51) Int. Cl.
*A61B 18/12*     (2006.01)
*H01P 5/103*     (2006.01)
(Continued)

(52) U.S. Cl.
CPC ............. *A61B 18/12* (2013.01); *A61B 18/18* (2013.01); *A61B 18/1815* (2013.01);
(Continued)

(58) Field of Classification Search
CPC ..... A61B 18/12; A61B 18/1815; A61B 18/22; A61B 1/00114; A61B 2017/00477;
(Continued)

(56) References Cited

U.S. PATENT DOCUMENTS 2,439,235 A     4/1948  Brown
2,678,835 A     5/1954  Clark, Jr.
(Continued)

FOREIGN PATENT DOCUMENTS

GB     2487199 A       7/2012
JP     57-203488 U    12/1982
(Continued)

OTHER PUBLICATIONS

Communication from the Japanese Patent Office in counterpart application No. 2017-520498, dated Jul. 30, 2019.
(Continued)

*Primary Examiner* — Eun Hwa Kim
*Assistant Examiner* — Catherine Premaj
(74) *Attorney, Agent, or Firm* — ArentFox Schiff LLP

(57) ABSTRACT

Embodiments of the invention provide a hollow cable for conveying radiofrequency and/or microwave frequency energy to an electrosurgical instrument that can fit within, e.g. slide relative to, the hollow cable. The hollow cable provides a bipolar electrical connection to the electrosurgical instrument that is maintained when the electrosurgical instrument is rotated relative to the hollow cable. The cable may comprise a hollow coaxial transmission line having a rotatable component mounted at its distal end. The rotatable component comprises a longitudinal passageway continuous (Continued)

with the hollow coaxial transmission line. The rotatable component is rotatable relative to the transmission line and comprises a first and second conductive portions that are respectively electrically connected to first and second terminals on the coaxial transmission line and which are configured to maintain an electrical connection with their respective terminal when rotated relative to the coaxial transmission line.

49 Claims, 10 Drawing Sheets

(51) Int. Cl.
*A61B 18/18* (2006.01)
*H01P 1/06* (2006.01)
*H01P 3/06* (2006.01)
*H01B 9/00* (2006.01)
*A61B 18/22* (2006.01)
*A61B 1/00* (2006.01)
*A61B 17/00* (2006.01)
*A61B 18/00* (2006.01)

(52) U.S. Cl.
CPC ............ *A61B 18/22* (2013.01); *H01B 9/003* (2013.01); *H01B 9/006* (2013.01); *H01P 1/067* (2013.01); *H01P 3/06* (2013.01); *H01P 5/103* (2013.01); *A61B 1/00114* (2013.01); *A61B 2017/00477* (2013.01); *A61B 2018/00065* (2013.01); *A61B 2018/126* (2013.01); *A61B 2562/22* (2013.01); *A61B 2562/225* (2013.01)

(58) Field of Classification Search
CPC .... A61B 2018/00065; A61B 2018/126; A61B 2562/22; A61B 2562/225; H01P 1/067; H01P 3/06; H01P 5/103
See application file for complete search history.

(56) References Cited

U.S. PATENT DOCUMENTS

| | | | | |
|---|---|---|---|---|
| 5,563,376 A | * | 10/1996 | Hansell, III | ....... H01B 11/1895 156/53 |
| 2008/0015570 A1 | * | 1/2008 | Ormsby | ............ A61B 18/1492 606/41 |
| 2010/0286707 A1 | * | 11/2010 | Griego | ............ A61B 17/32056 606/113 |
| 2011/0054446 A1 | * | 3/2011 | Schultz | .............. A61B 18/1492 604/528 |
| 2011/0201232 A1 | | 8/2011 | Islam | |
| 2013/0115784 A1 | * | 5/2013 | Gobel | .................. H01R 24/542 439/13 |
| 2013/0183856 A1 | | 7/2013 | Wild et al. | |

FOREIGN PATENT DOCUMENTS

| | | |
|---|---|---|
| JP | 2002-113020 A | 4/2002 |
| JP | 2002-177295 A | 6/2002 |
| JP | 2010-540029 A | 12/2010 |
| JP | 2014-511190 A | 5/2014 |
| WO | WO 2009/039093 A2 | 3/2009 |
| WO | WO 2013/179046 A2 | 12/2013 |

OTHER PUBLICATIONS

International Search Report of related International Patent Application No. PCT/EP2015/074047 dated Apr. 14, 2016.
Written Opinion of related International Patent Application No. PCT/EP2015/074047 dated Apr. 14, 2016.

* cited by examiner

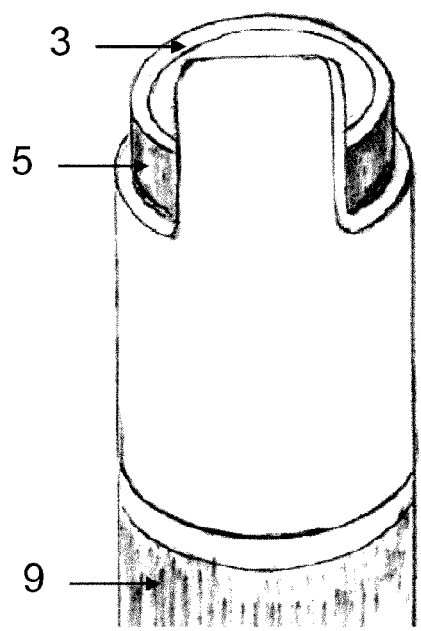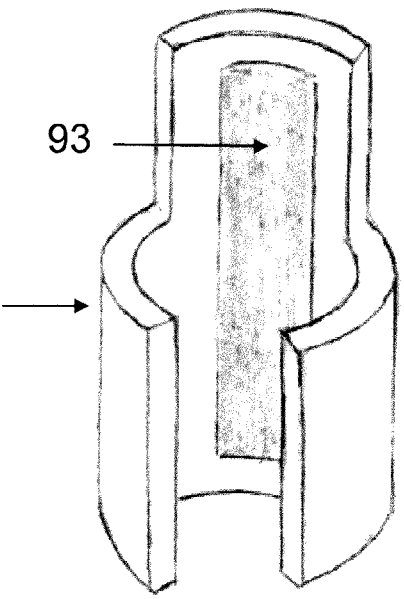
FIG. 12B  FIG. 12C
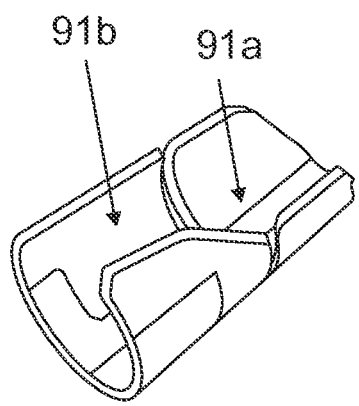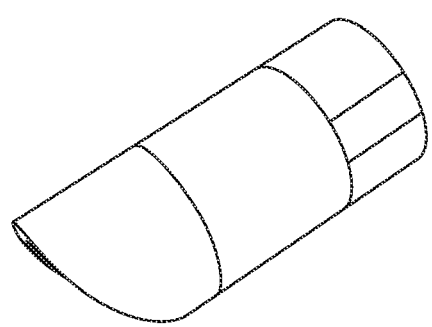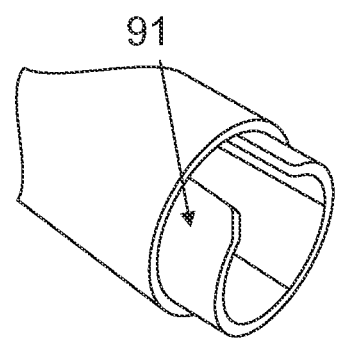
FIG. 12D  FIG. 12E  FIG. 12F

CABLE FOR CONVEYING RADIOFREQUENCY AND/OR MICROWAVE FREQUENCY ENERGY TO AN ELECTROSURGICAL INSTRUMENT

CROSS-REFERENCE TO RELATED APPLICATIONS

This application is a National Stage Entry of International Patent Application No. PCT/EP2015/074047, filed Oct. 16, 2015, which claims priority to Great Britain Patent Application No. 1418486.5, filed Oct. 17, 2014. The disclosures of the priority applications are incorporated in their entirety herein by reference.

FIELD OF THE INVENTION

The present invention relates to a cable for conveying radiofrequency and/or microwave frequency energy to an electrosurgical instrument. More particularly, the present invention relates to such a cable that comprises a hollow tube and wherein an electrosurgical instrument connected to the cable can be rotated relative to the cable.

BACKGROUND TO THE INVENTION

Electrosurgical instruments are instruments that are used to deliver radiofrequency and/or microwave frequency energy to biological tissue, for purposes such as cutting biological tissue or coagulating blood. Radiofrequency and/or microwave frequency energy is supplied to the electrosurgical instrument using a cable. Conventional cables used for this purpose have a coaxial transmission line structure comprising a solid cylindrical inner conductor, a tubular layer of dielectric material around the inner conductor, and a tubular outer conductor around the dielectric material.

When operating many electrosurgical instruments it is common to need to provide additional supplies or components (e.g. control means) to the electrosurgical instrument, such as a liquid or gas feed, liquids or gasses, or guide- or pull-wires for manipulating (for example opening/closing, rotating or extending/retracting) part(s) of the electrosurgical instrument.

In order to provide these additional supplies or components to the electrosurgical instrument, additional structures have been provided together with the conventional cable, such as additional tubes adjacent to the conventional cable. For example, it is known to provide an additional tube housing a pull-wire for the electrosurgical instrument alongside the conventional cable, and to house the conventional cable and the tube housing the pull-wire within a single protective jacket/casing.

SUMMARY OF THE INVENTION

The present inventors have realised that conventional cables for conveying radiofrequency and/or microwave energy to an electrosurgical instrument, which have the coaxial transmission line structure described above, suffer from various disadvantages.

In particular, the present inventors have realised that with a conventional arrangement for providing everything needed by the electrosurgical instrument in use, which includes a conventional cable and other structures such as an additional tube for housing a pull-wire, significant amounts of space are wasted, and for a given overall size (diameter) of the arrangement the maximum possible size (diameter) of the cable is limited, which may lead to significant power losses occurring in the cable.

Furthermore, the present inventors have realised that with the conventional arrangement, additional components such as pull-wires are positioned towards the edges of the arrangement, and this off-centre configuration may cause problems when operating the electrosurgical instrument using the additional components.

The present inventors have realised that one or more of these problems may be addressed by providing a cable that is hollow, so that one or more additional components can be passed through the cable in use. By positioning one or more of the additional components inside the cable, the size (diameter) of the cable can be maximised, which may reduce power losses occurring in the cable, because less space around the cable is required for additional structures. Furthermore, by positioning an additional component such as a pull-wire inside the cable, it may be possible to deliver actuation to the electrosurgical instrument down (or closer to) the centre of the cable, which may improve the actuation of the electrosurgical instrument.

The present inventors have also realised that such a hollow cable is achievable in practice because of the skin-depth effect when transmitting microwave frequency energy, which means that microwave frequency energy travels only in a shallow surface area of a conductor. The present inventors have also realised that radiofrequency energy can be suitably conveyed along such a hollow cable, despite the use of thin conductors in such a cable increasing the resistance, loss and heating in the cable compared to the use of thicker conductors.

Furthermore, the present inventors have realised that it is desirable to provide such a cable with which it is possible to rotate an electrosurgical instrument that is connected to the cable relative to the cable. Enabling relative rotation between the electrosurgical instrument and the cable may allow more suitable control of the electrosurgical instrument during operation of the electrosurgical instrument, for example by allowing more accurate or appropriate positioning or orientation of part or all of the electrosurgical instrument.

Therefore, at its most general the present invention provides a hollow cable for conveying radiofrequency and/or microwave frequency energy to an electrosurgical instrument, wherein a bipolar electrical connection to the electrosurgical instrument is configured so that the bipolar electrical connection is maintained when the electrosurgical instrument is rotated relative to the cable.

According to a first aspect of the present invention there is provided a cable for conveying radiofrequency and/or microwave frequency energy to an electrosurgical instrument at a first end of the cable, the cable comprising:

a hollow tube comprising inner and outer electrically conductive layers separated by dielectric material to form a transmission line;

a first terminal at the first end of the cable for forming an electrical connection to the inner conductive layer;

a second terminal at the first end of the cable for forming an electrical connection to the outer conductive layer;

a rotatable component at the first end of the cable, wherein the rotatable component comprises a longitudinal passageway continuous with the hollow tube, and wherein the rotatable component is rotatable relative to the transmission line and comprises:

a first portion electrically connected to the first terminal, wherein the first portion and the first terminal are rotatable relative to each other and are configured to maintain an electrical connection when rotated relative to each other;

a second portion electrically connected to the second terminal, wherein the second portion and the second terminal are rotatable relative to each other and are configured to maintain an electrical connection when rotated relative to each other.

Thus, the cable can be connected to an electrosurgical instrument through the rotatable component (which may, for example, be connected to the electrosurgical instrument, directly or indirectly, or may be integral with the electrosurgical instrument) to form a bipolar electrical connection to the electrosurgical instrument. Furthermore, this bipolar electrical connection is maintained when the rotatable component (and therefore the electrosurgical instrument) is rotated, because the electrical connections between the first and second portions and the first and second terminals are maintained during rotation of the rotatable component.

The longitudinal passageway of the rotatable component may comprise an open channel, i.e. in which at least a part of the circumference of the channel is uncovered, or a closed channel, for example a bore or lumen. The longitudinal passageway may be continuous with the hollow tube by being positioned at the first end of the hollow tube so that components fed through the hollow tube and out of the first end of the hollow tube are also fed through the longitudinal passageway. The longitudinal passageway may be aligned with a central passageway of the hollow tube. Alternatively, some or all of the longitudinal passageway may be continuous with the hollow tube by some or all of the longitudinal passageway overlapping a central passageway of the hollow tube, for example by some or all of the rotatable component being positioned around or inside the hollow tube.

In some embodiments, the cable may be for conveying only radiofrequency energy to the electrosurgical instrument. In other embodiments, the cable may be for conveying only microwave frequency energy to the electrosurgical instrument. In further embodiments, the cable may be for conveying both radiofrequency energy and microwave frequency energy to the electrosurgical instrument.

The term inner means closer to a centre of the hollow tube. The term outer means further from a centre of the hollow tube.

The tube may be a cylindrical tube in which the inner conductive layer and the outer conductive layer are concentric (coaxial) layers. In this case, the term inner means radially inner, and the term outer means radially outer.

The term hollow means that the tube has a bore or lumen extending along its length, for example centred on a centre of the tube.

The term conductive is used in the present invention to mean electrically conductive, unless the context dictates otherwise.

An electrosurgical instrument may be any instrument, or tool, which is used during surgery and which utilises radiofrequency or microwave frequency energy. Herein, radiofrequency (RF) may mean a stable fixed frequency in the range 10 kHz to 300 MHz and microwave energy may mean electromagnetic energy having a stable fixed frequency in the range 300 MHz to 100 GHz. The RF energy should have a frequency high enough to prevent the energy from causing nerve stimulation and low enough to prevent the energy from causing tissue blanching or unnecessary thermal margin or damage to the tissue structure. Preferred spot frequencies for the RF energy include any one or more of: 100 kHz, 250 kHz, 400 kHz, 500 kHz, 1 MHz, 5 MHz. Preferred spot frequencies for the microwave energy include 915 MHz, 2.45 GHz, 5.8 GHz, 14.5 GHz, 24 GHz.

The hollow nature of the cable means other components needed in use of the electrosurgical instrument, such as a gas or liquid feed, or a pull-wire or other control means, can be fed up through the inside of the cable. This means the outer diameter of the cable can be maximised relative to an arrangement in which the other components have to be positioned around the outside of the cable. Maximising the diameter of the cable reduces power losses in the cable relative to a smaller diameter cable. The cable may therefore be able to deliver more power to the electrosurgical instrument relative to a conventional cable. Furthermore, actuating components such as pull-wires may be positioned close to a centre of the cable, which may improve actuation of the electrosurgical instrument.

Additional components, such as actuating controls or gas or liquid feeds, that are passed through the hollow tube of the cable may be arranged in a concentric arrangement in the hollow tube of the cable. This may optimise the use of space in the hollow tube of the cable. This may also facilitate rotation of the rotatable component and the electrosurgical instrument at the first end of the cable, because it will reduce or prevent tangling of the additional components within the hollow tube of the cable during the rotation.

The transmission line may be a coaxial transmission line in which the inner and outer conductive layers are coaxial.

The first end of the cable is the end of the cable that is for connecting (either directly or indirectly through another component or part) to the electrosurgical instrument. In other words, the first end of the cable is the distal end of the cable.

The opposite, second end of the cable is for connecting the cable to a generator for supplying radiofrequency and/or microwave frequency energy to the cable. In other words, the second end of the cable is the proximal end of the cable. The second end of the cable may have a terminal or connector for connecting the second end of the cable to a generator. Thus, the cable may be for conveying radiofrequency and/or microwave frequency energy from a generator connected to the second (proximal) end of the cable to an electrosurgical instrument connected to the first (distal) end of the cable.

The first terminal may comprise an end of the inner conductive layer, for example an end of the inner conductive layer exposed on a face of the cable at the first end of the cable, or a circumferential surface of the inner conductive layer at the end of the inner conductive layer.

The second terminal may comprise an end of the outer conductive layer, for example an end of the outer conductive layer exposed on a face of the cable at the first end of the cable, or a circumferential surface of the outer conductive layer at the end of the outer conductive layer.

An electrical connection between a terminal and a corresponding portion at its most general means an interface between the terminal and the corresponding portion where an electrical signal can be passed from the terminal to the corresponding portion. For example, there may be direct contact between the terminal and the corresponding portion so that current flows directly between them, or an indirect galvanic connection through an intermediate conductive material or medium, for example a conductive adhesive or bonding material. Alternatively, an electrical signal may be passed from the terminal to the corresponding portion through some other type of electrical coupling, for example inductive or capacitive coupling, or other types of magnetic and/or electrical coupling, for example a transformer.

The cable according to the first aspect of the present invention may have any one, or, to the extent that they are compatible, any combination of the following optional features.

The first portion or the second portion may be configured to maintain the electrical connection to the respective terminal during relative rotation by being configured to remain in direct physical contact with the respective terminal during relative rotation.

The first terminal may comprise a surface of an exposed part of the inner conductive layer. The term exposed may mean uncovered, or accessible, for example on a circumferential surface of the cable. The surface of the exposed part of the inner conductive layer may be a circumferential surface of the exposed part of the inner conductive layer.

The exposed part of the inner conductive layer may comprise an exposed tubular part of the inner conductive layer. In other words, a short length of the tubular inner conductive layer may be exposed, for example at an end of the inner conductive layer. This may be achieved, for example, by not providing a covering layer, e.g. a tubular layer, on the surface of the inner conductive layer in this region.

The first terminal may be on an outer circumferential surface of the cable, and the first portion may be positioned around the outer circumferential surface of the cable. Thus, a surface (for example the inner or outer surface) of the first portion may be adjacent (opposite) to the first terminal, so that an electrical connection can readily be made between them.

Alternatively, the first terminal may be on an inner circumferential surface of the cable, and the first portion may be positioned inside the inner circumferential surface of the cable.

The first portion may comprise conductive material on an inner surface or an outer surface thereof, the conductive material being in contact with the first terminal. Thus, an electrical connection is formed between the first portion and the first terminal by conductive material on the first portion physically contacting the first terminal. Where the first portion is positioned inside a circumferential surface on which the first terminal is located, the conductive material will be on an outer surface of the first portion.

Alternatively, where the first portion is positioned around a circumferential surface on which the first terminal is located, the conductive material will be on an inner portion of the first surface.

The conductive material may comprise a circumferential band of conductive material. This may facilitate maintaining an electrical connection to the first terminal as the first portion is rotated.

In addition, or alternatively, the first portion may comprise one or more conductive elements biased into contact with the first terminal.

The one or more conductive elements may comprise a sprung wing, a sprung flap, a sprung pad or a sprung protrusion.

The one or more conductive elements may be made conductive by coating them in conductive material.

The one or more conductive elements may be positioned on an inner or an outer surface of the first portion.

Thus, a reliable sprung electrical connection may be provided between the first portion and the first terminal, which is maintained during relative rotation.

The first portion may comprise a hollow tube. This may facilitate rotationally mounting the first portion on the cable.

Where the first terminal is on an outer circumferential surface of the cable, and the first portion is positioned around the outer circumferential surface of the cable, the first portion may comprise first and second sprung wings gripping the outer circumferential surface of the cable there-between. Thus, a secure sprung electrical connection may be made between the first portion and the first terminal that is maintained during relative rotation of the first terminal and the first portion.

Where the first terminal is on an inner circumferential surface of the cable, and the first portion is positioned inside the inner circumferential surface of the cable, the first portion may comprise first and second sprung wings pressing outwards against the inner circumferential surface of the cable. Thus, a secure sprung electrical connection may be made between the first portion and the first terminal that is maintained during relative rotation of the first terminal and the first portion.

The first portion may comprise a hollow tube of naturally sprung material from which an axial strip has been removed from the circumference thereof to form the first and second sprung wings. Where the first portion is positioned around an outer circumferential surface of the cable, the hollow tube from which the first portion is made may have an initial diameter smaller than the diameter of the outer circumferential surface. Therefore, the sprung wings will be bent outwards when the first portion is positioned around the outer circumferential surface and the resulting spring force will cause the sprung wings to grip the cable there-between. Alternatively, where the first portion is positioned inside an inner circumferential surface of the cable, the hollow tube from which the first portion is made may have an initial diameter greater than the diameter of the inner circumferential surface. Therefore, the sprung wings will be bent inwards when the first portion is positioned inside the inner circumferential surface and the resulting spring force will cause the sprung wings to press outwards against the inner circumferential surface.

The advantages of the following features of the second terminal may be the same as the above advantages of the corresponding first terminal.

The second terminal may comprise a surface of an exposed part of the outer conductive layer.

The exposed part of the outer conductive layer may comprise an exposed tubular part of the outer conductive layer.

The second terminal may be on an outer circumferential surface of the cable, and the second portion may be positioned around the outer circumferential surface of the cable.

Alternatively, the second terminal may be on an inner circumferential surface of the cable, and the second portion may be positioned inside the inner circumferential surface of the cable.

The second portion may comprise conductive material on an inner surface or an outer surface thereof, the conductive material being in contact with the second terminal.

The conductive material may comprise a circumferential band of conductive material.

The second portion may comprise one or more conductive elements biased into contact with the second terminal.

The one or more conductive elements may comprise a sprung wing, a sprung flap, a sprung pad or a sprung protrusion.

The second portion may comprise a hollow tube.

When the second terminal is on an outer circumferential surface of the cable, and the second portion is positioned around the outer circumferential surface of the cable, the second portion may comprise first and second sprung wings gripping the outer circumferential surface of the cable there-between.

When the second terminal is on an inner circumferential surface of the cable, and the second portion is positioned inside the inner circumferential surface of the cable, the second portion may comprise first and second sprung wings pressing outwards against the inner circumferential surface of the cable.

The second portion may comprise a hollow tube of naturally sprung material from which an axial strip has been removed from the circumference thereof to form the first and second sprung wings.

The first portion may be connected to, or integral with, the second portion. For example, the first portion and the second portion may be moulded together, for example from an insulating material such as plastic, which is then selectively coated with conductive material. Alternatively, the first portion and the second portion may be formed, for example by laser cutting, from the same pipe. Alternatively, the first portion and the second portion may be made separately, and then connected together, for example by a friction fit or by fixing or bonding them together.

The present inventors have also realised that an alternative way of achieving rotation of an electrosurgical instrument relative to the cable is to make the inner conductive layer of the cable rotate with the electrosurgical instrument, so that there is relative rotation between the inner conductive layer and the outer conductive layer.

Therefore, according to a second aspect of the present invention there is provided a cable for conveying radiofrequency and/or microwave frequency energy to an electrosurgical instrument, the cable comprising:

a first part comprising an outer conductive layer provided on an outer side of a hollow tube of dielectric material;

a second part comprising an inner conductive layer;

wherein the second part is positioned inside the first part so that the inner conductive layer and the outer conductive layer form a transmission line;

wherein the second part is rotatable relative to the first part;

wherein the second part comprises a further conductive layer that is electrically connected to the outer conductive layer in a region where the outer conductive layer is exposed, the further conductive layer being electrically isolated from the inner conductive layer, wherein the further conductive layer and the outer conductive layer are rotatable relative to each other and are configured to maintain an electrical connection when rotated relative to each other.

Thus, a bipolar electrical connection can be made to an electrosurgical instrument connected to the second part and maintained during rotation of the electrosurgical instrument (and the second part), because the inner conductive layer has a fixed connection to the second part, and because the electrical connection between the second part and the first part is maintained during relative rotation between the second part and the first part.

The second part may also comprise an inner hollow tube of material, and the inner conductive layer may be provided on an outer side of the inner hollow tube of material, for example by being coated on an outer surface of the inner hollow tube or material. In some embodiments, the inner conductive layer may be a solid conductive tube.

This arrangement has an advantage that the second part can be moved axially relative to the first part in addition to being rotatable relative to the first part. Thus, it may be possible to more accurately position or orientate the second part (and thus the electrosurgical instrument).

The first and/or second aspects of the present invention may have any one, or, if to the extent they are compatible, any combination of the following optional features.

The cable may comprise an actuating means fed through the hollow tube of the cable for rotating the rotatable component relative to the transmission line, or for rotating the second part relative to the first part.

The actuating means may comprise an actuator element such as a rod, wire, cable or hollow tube. Alternatively, the actuating means may comprise a fluid, for example a liquid or gas, for example in a hydraulic actuation system.

In one embodiment, the electrosurgical instrument may be rotated by connecting (fixing) the actuator element to the electrosurgical instrument and by rotating the actuator to directly rotate the electrosurgical instrument. This may provide acceptable rotational control of the electrosurgical instrument in some circumstances.

However, the present inventors have realised that in some cases this type of control may lead to rotation of the electrosurgical instrument occurring in a series of jumps (or jolts) or intermittent sudden changes, which may be undesirable in many applications. This is believed to be because of bends in the actuator causing friction and torque pressures during rotation of the actuator.

The present inventors have realised this problem may be overcome by causing rotation of the electrosurgical instrument by pushing or pulling an actuator element such as a rod, wire, cable, tube or pipe, to move it axially relative to the electrosurgical instrument, and by providing an interface between the actuator and the electrosurgical instrument that converts this axial movement into a rotational movement of the electrosurgical instrument. The present inventors have realised that axial pulling and pushing movements of an actuator may be smoothly transmitted along the cable, even where the cable is bent, so that smooth rotation of the electrosurgical instrument can be achieved.

Therefore, the actuating means may be configured to be moved axially along the hollow tube of the cable, and the cable may comprise an interface provided in the hollow tube of the cable for converting axial movement of the actuating means into rotational movement of the rotatable component or the second part (and thus of the electrosurgical instrument). In other words, the actuating means may be pushed or pulled (retracted) along the cable. With a fluid, the same effect may be achieved by changes in pressure or pushing forces applied to the fluid.

A further interface may be provided to prevent the actuator element from rotating relative to the cable, so that the actuator element is only able to move axially along the cable.

The actuator element may have a helical path provided on an outer surface thereof, and the cable may comprise a rotator having a follower that follows the helical path when the actuator element is moved axially, thereby causing the rotator to rotate. Thus, axial movement of the actuator element is converted into rotational movement of the rotator.

Alternatively, the actuator element may comprise a follower on an outer surface thereof, and the cable may comprise a rotator having a helical path provided on an inner surface thereof along which the follower travels when the actuator element is moved axially, thereby causing the rotator to rotate. Thus, axial movement of the actuator element is converted into rotational movement of the rotator.

The rotator may be a hollow cylindrical body or tubular body.

The helical path may comprise a raised helical path.

Alternatively, the helical path may comprise a helical channel, a helical groove, or a helical slot.

The follower may comprise: a protrusion; a pin; a fin; a recess; a groove; a channel; or a slot.

The rotator may be connected to (either directly or indirectly through another part or component), or integral with, the electrosurgical instrument, so that rotation of the rotator causes rotation of the electrosurgical instrument.

When the cable comprises the rotatable component, the rotator may be connected to (either directly or indirectly through another part or component), or integral with, the rotatable component, so that rotation of the rotator causes rotation of the rotatable component.

In one embodiment, the interface for preventing the actuator from rotating relative to the cable may comprise a follower (for example a pin or fin) on the actuator that follows a linear axial path (for example a groove or slot) on a wall of the cable or of a handle of the cable. Alternatively, the interface may comprise a follower (for example a pin or fin) on the cable or a handle of the cable that is follows a linear axial path (for example a groove or slot) on the surface of the actuator. In either case, the actuator is able to move axially relative to the cable but is prevented from rotating relative to the cable.

The cable may be configured to convey radiofrequency energy to the electrosurgical instrument with the transmission line and a further conductor positioned in the hollow tube and extending along the hollow tube, and the further conductor may be electrically insulated from the transmission line within the hollow tube of the cable.

A possible problem with transmitting both radiofrequency energy and microwave frequency energy down the same transmission line of the cable is that the high voltage radiofrequency energy may cause breakdown of the dielectric material, particularly in porous, low loss materials that are particularly suitable for use in conveying microwave frequencies. Therefore, in some embodiments the radiofrequency signal may instead be conveyed using the transmission line and a conductor positioned in the hollow tube and extending along the hollow tube. This may significantly reduce the risk of breakdown of the dielectric material.

The cable may be configured to convey radiofrequency energy in this way by having a terminal or connector at its second (proximal) end for connecting to a generator for supplying radiofrequency energy to the further conductor and the transmission line.

Electrically insulating the further conductor from the transmission line within the hollow cable may prevent electrical breakdown of air between the further conductor and the transmission line, which would otherwise damage the cable or increase the power loss in the cable. This may be achieved with an insulating layer around the further conductor (e.g. provided on a surface of the further conductor) or an insulating layer provided on an innermost surface of the cable, for example.

The cable may be configured to convey radiofrequency energy to the electrosurgical instrument with (only) the inner conductive layer and the further conductor, or with (only) the outer conductive layer and the further conductor, or with the inner conductive layer, the outer conductive layer, and the further conductor, wherein the inner conductive layer and the outer conductive layer are electrically connected at the second (proximal) end of the cable.

The conductor positioned in the hollow tube may be a conductive rod or tube used specifically for this purpose. Alternatively, the further conductor may comprise a further tubular conductive layer of the cable, for example an innermost tubular layer of the cable. Alternatively, an additional component being passed through the hollow tube may be function as the central conductor. For example, a tube used to supply liquid or gas to the electrosurgical instrument, or a housing for a guide- or pull-wire may be formed of, or coated with, a conducting material and may act as the central conductor. A generator may then be used to input the radiofrequency signal into the cable using the transmission line and the further conductor separately from the microwave frequency signal, which is input to the inner and outer conductive layers of the transmission line only.

With an arrangement such as this it may be necessary to provide a configuration, such as a diplexer, at the first end of the cable to prevent the higher voltage radiofrequency signal from travelling back along the inner and outer conductors, and/or to prevent the microwave signal from travelling back along the further conductor. Alternatively, the further conductor may be configured so that it can be physically disconnected when using the cable to only convey microwave energy. For example, this may be achieved by pulling the further conductor axially away from the electrosurgical instrument so that it is no longer in contact with a corresponding terminal of the electrosurgical instrument.

The cable may comprise a conductor positioned in the hollow tube and extending along the hollow tube for conveying radiofrequency energy to the electrosurgical instrument with the transmission line.

The dielectric material may comprise a solid tube of dielectric material; or a tube of dielectric material having a porous structure. Being a solid tube of dielectric material may mean that the dielectric material is substantially homogeneous. Having a porous structure may means that the dielectric material is substantially inhomogeneous, with a significant number or amount of air pockets or voids.

For example, a porous structure may mean a honeycomb structure, a mesh structure, or a foam structure.

The dielectric material may comprise PTFE, or another low-loss microwave dielectric.

The dielectric material may comprise a tube with a thickness of greater than 0.2 mm, for example a tube with a thickness of 0.3 mm or 0.4 mm. In one embodiment, the dielectric material may be a tube of PTFE having an inner diameter of 1.6 mm and an outer diameter of 2.4 mm, for example.

The inner conductive layer and/or the outer conductive layer may comprise: a conductive coating on the inside or outside of a tube of material; a solid tube of conductive material positioned against the inside or outside of a tube of material; or a layer of braided conductive material formed on, or embedded in, a tube of material.

The conductive coating or the conductive material may be a metal, such as silver, gold or copper. Alternatively, the conductive coating or the conductive material may comprise a different type of conductive material, such as graphene. The conductive coating and the conductive material are preferably good conductors, i.e. low loss conductors at microwave frequencies or radiofrequencies, for example not steel.

The inner and/or the outer conductive layer may comprise a silver coating.

The inner and/or the outer conductive layer may have a thickness of approximately 0.01 mm.

Where the cable is for conveying only radiofrequency energy to the electrosurgical instrument and not microwave frequency energy, it is not necessary for the dielectric material to be a good microwave dielectric. Instead, in these embodiments the dielectric material may be a good radiofrequency dielectric material, for example a material that provides a stand-off or break down voltage that is sufficiently greater than the voltage of the radiofrequency signal, i.e. a material that has a sufficiently high dielectric strength. The dielectric material may also be selected at least in part based on its mechanical properties, such as its hardness, strength, or ease of plating. A suitable material may be Kapton, for example Kapton Polyimide film which has a breakdown strength of around 3000 KV/mm. Thus, in the following PTFE may be replaced with Kapton or Kapton Polyimide or another suitable radiofrequency dielectric when the cable is to be used for conveying only radiofrequency energy to the electrosurgical instrument.

Where only radiofrequency energy is being conveyed, reflection of energy due to impedance mismatch at the region where the cable is connected to the electrosurgical instrument is less significant that when conveying microwave frequency energy. Thus, it may be simpler to connect the cable to the electrosurgical instrument, and this could be achieved for example with two appropriate connected wires (in addition to the connection arrangements discussed below).

In some embodiments, a single conductor monopolar tool may be introduced into the cable and connected to the inner conductive layer only.

A protective covering or liner may be provided on an inner side of the inner metal layer to protect the inner metal layer, for example from damage caused by components or tools being passed through the hollow cable. In one embodiment, the protective liner may comprise an inner tubular layer, and the inner metal layer may be coated on an outer surface of the inner tubular layer. The inner tubular layer may comprise an insulating material, or a dielectric material.

In one embodiment, the first end of the cable may be detachable or otherwise separable from the remainder of the cable, for example so that different first ends having different configurations of the first and second terminals may be used with the same cable by attaching them to the cable. In another embodiment, the first end of the cable may be integral or fixed to the cable.

A protective outer sheath or outer coating (for example a spray coating) may be present on an outer surface of the cable, to protect the outer surface of the cable. This may comprise an insulating material for example, and/or a material chosen for its mechanical properties, such as strength and/or hardness.

In one configuration the cable may comprise a hollow inner tubular layer; a tube of the inner conductive layer on an outer surface of the hollow inner tubular layer; a tube of the dielectric material on an outer surface of the tube of the inner conductive layer; and a tube of the outer conductive layer on an outer surface of the tube of the dielectric material. The structure may, or may not, comprise air gaps between some or all of these layers. An advantage of avoiding air gaps is that losses in the cable may be minimised. In one example, this structure could be manufactured by sequentially coating each subsequent layer over the preceding (inner) layer. Alternatively, this structure could be made by forming one or more of the layers as a first part and one or more of the layers as a second part, and then sliding one part inside of the other. The hollow inner tubular layer may comprise PTFE or Polyimide. The hollow inner tubular layer may have a thickness of 0.1 mm.

The inner conductive layer may protrude beyond an edge of the tubular dielectric material, so that the inner conductive layer is exposed at the first end of the cable. This may facilitate connection of the electrosurgical instrument at the first end of the cable.

In an alternative configuration the cable may comprise a hollow tube of the inner conductive layer; a tube of the dielectric material on an outer surface of the hollow tube of the inner conductive layer; and a tube of the outer conductive layer on an outer surface of the tube of the dielectric material. Again, air gaps may, or may not, be present between one or more of the layers. In one example, such a configuration may be manufactured by coating the inner and outer conductive layers on the inner and outer surfaces of the dielectric material, respectively.

This cable may further comprise a protective outer tubular layer on an outer surface of the tube of the outer conductive layer. The outer tubular layer may comprise PTFE or Polyimide. The protective outer tubular layer may be an insulating layer.

The outer conductive layer may protrude beyond an edge of the tube of dielectric material, so that the outer conductive layer is exposed at the first end of the cable. This may facilitate connection of the electrosurgical instrument.

An outer diameter of the cable may be smaller over a portion (section or part) of its length adjacent to the first end of the cable. In other words, the cable may be narrower at the first end. This may facilitate connection of the cable to the electrosurgical instrument.

The outer diameter of the cable may be made smaller over the portion by reducing an internal diameter of cable. In other words, the walls of the cable may be jogged or moved inwards so that they are closer to the central axis of the cable for a section of the cable at the first end.

Alternatively, or in addition, the outer diameter of the cable may be made smaller over the portion by reducing a thickness of the dielectric material, or another component of the cable. In this case, the internal diameter of the cable may be unchanged, but the external diameter is reduced. The thickness of the dielectric material, or the other component, may be reduced by machining the region down to a smaller thickness, or by using a heat-shrink material, for example.

Radiofrequency energy and/or microwave frequency energy may be input to the cable using a side feed positioned at, or adjacent to, the second (proximal) end of the cable. This may allow a clear channel through the cable for various other components and instrument controls. In order that RF energy is not short circuited, the inner and outer conductive layers may not be connected across the dielectric material where the hollow channel exits the cable. Microwave energy may be prevented from leaking from the open end of the cable by a coaxial filter or choke. The distance of the choke or filter from the side feed may be chosen in order to match the impedance of the generator equipment to the impedance of the hollow cable and side feed.

BRIEF DESCRIPTION OF THE DRAWINGS

Embodiments of the present invention will now be discussed, by way of example only, with reference to the accompanying Figures, in which:

FIGS. 12A to 12F are schematic illustrations of a concept according to an embodiment of the present invention for forming a rotating electrical connection to a tubular layer of metal;

DETAILED DESCRIPTION; FURTHER OPTIONS AND PREFERENCES

Figure 1:
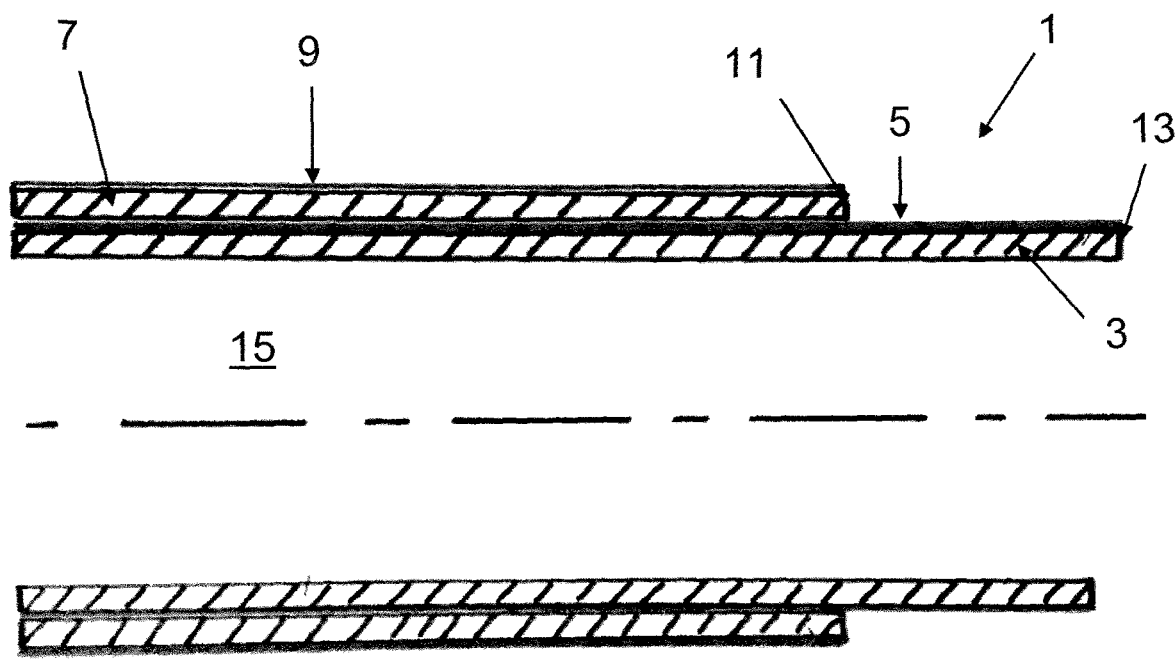
FIG. 1 is a schematic illustration of a part of a cable according to an embodiment of the present invention.

Where features of the embodiments described below are equivalent, the same reference numerals are used and detailed description thereof is not repeated.

A schematic illustration of a part of a cable according to an embodiment of the present invention is illustrated in FIG. 1. FIG. 1 only shows selected details of the cable relating to its general construction, and does not show the connection to an electrosurgical instrument. The dashed line in FIG. 1 is intended to illustrate a central axis of the cable.

The cable 1 illustrated in FIG. 1 comprises an inner tubular layer 3, which may comprise PTFE or Polyimide or another material that provides sufficient mechanical strength (the electrical properties of this layer are of less significance). In this embodiment, the inner tubular layer has a thickness of 0.1 mm.

An inner metal layer 5 (which corresponds to an inner conductive layer) is provided on an outer surface of the inner tubular layer 3, to form a tube around the inner tubular layer 3. In this embodiment, the inner metal layer 5 is made of silver and has a thickness of 0.01 mm.

A dielectric layer 7 (which corresponds to dielectric material) is provided on an outer surface of the inner metal layer 5, to form a tube around the inner metal layer 5. In this embodiment, the dielectric layer 7 comprises PTFE and has a thickness of 0.4 mm.

An outer metal layer 9 (which corresponds to an outer conductive layer) is provided on an outer surface of the dielectric layer 7, to form a tube around the dielectric layer 7. In this embodiment, the outer metal layer 9 is made of silver and has a thickness of 0.01 mm.

Of course, in other embodiments the thicknesses of any of the layers may be different to the thicknesses described above, and the material of any of the layers may also be different. For example, the dielectric layer 7 may comprise a different low-loss microwave dielectric material, or a different radiofrequency dielectric material, instead of PTFE, and the inner and/or outer metal layers 5, 9 may be formed of metal(s) other than silver.

The inner metal layer 5, dielectric layer 7 and outer metal layer 9 form a coaxial transmission line for conveying radiofrequency and/or microwave frequency energy to an electrosurgical instrument connected thereto.

The inner tubular layer 3 may act to protect the inner metal layer 5 from any components inserted through the hollow inner of the cable 1 during use of the cable. In this sense, the inner tubular layer may be considered to be a liner. The inner tubular layer 3 may also provide mechanical strength to the cable.

In other embodiments, a further insulating sleeve or coating may be provided on an outer surface of the outer metal layer 9 to prevent wear of the outer metal layer 9 during use of the cable, and to electrically insulate the outer metal layer 9.

An edge 11 of the dielectric layer 7 (and the outer metal layer 9) is set back relative to an edge 13 of the inner tubular layer 3 (and the inner metal layer 5), so that a region of the inner metal layer 5 is exposed between the edges 11, 13. This may facilitate connection of an electrosurgical instrument at the end of the cable.

In some embodiments, the edge of the outer metal layer 9 may be set back relative to the edge 11 of the dielectric layer 7, in order to increase an air gap between the outer metal layer 9 and the inner metal layer 5. This may reduce the risk of electrical breakdown of the air between the outer metal layer 9 and the inner metal layer 5 occurring.

Alternatively, or in addition, in some embodiments an insulating fluid or grease or other material may be applied at or around the edge of the outer metal layer 9, and/or in other areas of the cable, to reduce the risk of electrical breakdown of air occurring in the cable.

In one embodiment, the structure shown in FIG. 1 may be constructed by sequentially forming each layer on an outer surface of the previous (inner) layer. For example, an outer surface of the inner tubular layer 3 may be coated with metal to form the inner metal layer 5. The set back position of the edge 11 may be achieved by machining this edge back, for example. Alternatively, this configuration may be manufactured by forming the inner metal layer 5 on an outer surface of the inner tubular layer 3, forming the outer metal layer 9 on an outer surface of the dielectric layer 7, and then inserting the inner tubular layer 3 inside the dielectric layer 7.

The cable shown in FIG. 1 has a central channel, bore or lumen 15 through which components, such as a liquid or gas feed, or a pull-wire or other control means, can be fed and supplied to an electrosurgical instrument connected to the cable.

Figure 2:
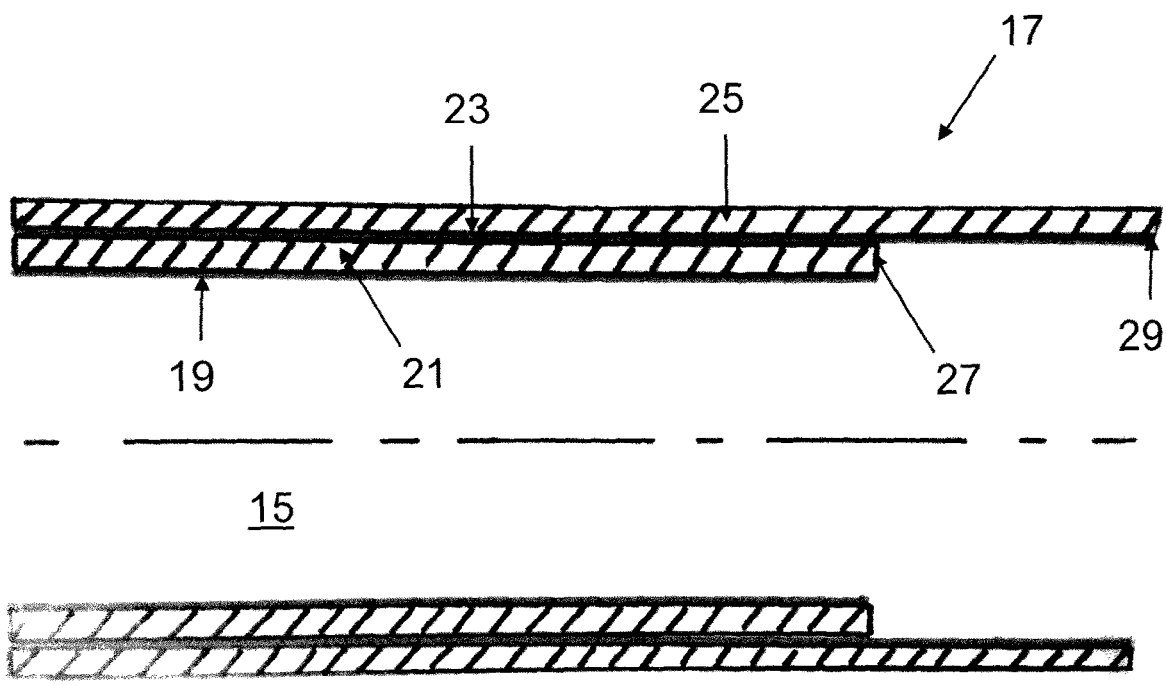
FIG. 2 is a schematic illustration of a part of a cable according to an alternative embodiment of the present invention.

A schematic illustration of a part of a cable according to an alternative embodiment of the present invention is illustrated in FIG. 2. FIG. 2 only shows selected details of the cable relating to its general construction, and does not show the connection to the electrosurgical instrument. The dashed line in FIG. 2 is intended to illustrate a central axis of the cable.

The cable 17 illustrated in FIG. 2 comprises an inner tubular metal layer 19 (which corresponds to an inner conductive layer). In this embodiment, the inner tubular metal layer 19 is made of silver and has a thickness of 0.01 mm.

A dielectric layer 21 (which corresponds to dielectric material) is provided on an outer surface of the inner tubular metal layer 19, to form a tube around the inner tubular metal layer 19. In this embodiment, the dielectric layer 21 comprises PTFE and has a thickness of 0.4 mm.

An outer metal layer 23 is provided on a surface of the dielectric layer 21. In this embodiment the outer metal layer 23 comprises silver and has a thickness of 0.01 mm.

An outer tubular layer 25 is provided on a surface of the outer metal layer 23. In this embodiment the outer tubular layer 25 comprises PTFE or Polyimide and has a thickness of 0.1 mm.

Of course, in other embodiments the thicknesses of any of the layers may be different to the thicknesses described above, and the material of any of the layers may also be different. For example, the dielectric layer 21 may comprise a different low-loss microwave dielectric material, or a different radiofrequency dielectric, instead of PTFE, and the inner and/or outer metal layers 19, 23 may be formed of metal(s) other than silver.

The inner metal layer 19, dielectric layer 21 and outer metal layer 23 form a coaxial transmission line for conveying radiofrequency and/or microwave frequency energy to an electrosurgical instrument connected thereto.

An edge 27 of the dielectric layer 21 (and the inner metal layer 19) is set back relative to an edge 29 of the outer metal layer 23 (and the outer tubular layer 25), so that a region of the outer metal layer 23 is exposed between the edges 27, 29. This may facilitate connection of an electrosurgical instrument at the end of the cable.

In one embodiment, this structure may be manufactured by sequentially coating each layer on the preceding (inner) layer. The set back position of the edge 27 may be achieved by machining this edge back, for example. Alternatively, this structure may be manufactured by forming the inner metal layer 19 on an inner surface of the dielectric layer 21, forming the outer metal layer 23 on an inner surface of the outer tubular layer 25, and then inserting the dielectric layer 21 inside the outer tubular layer 25

Figure 3:
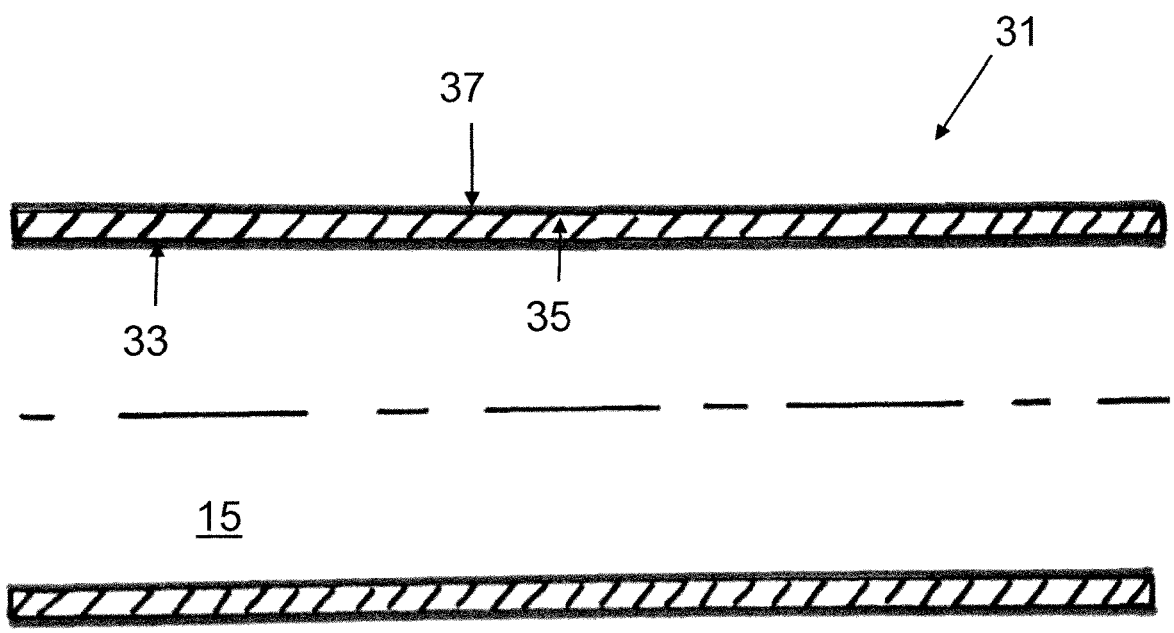
FIG. 3 is a schematic illustration of a part of a cable according to an alternative embodiment of the present invention.

A schematic illustration of a part of a cable according to an alternative embodiment of the present invention is illustrated in FIG. 3. FIG. 3 only shows selected details of the cable relating to its general construction, and does not show the connection to the electrosurgical instrument. The dashed line in FIG. 3 is intended to illustrate a central axis of the cable.

The cable 31 illustrated in FIG. 3 comprises an inner tubular metal layer 33 (which corresponds to an inner conductive layer). In this embodiment, the inner tubular metal layer 33 is made of silver and has a thickness of 0.01 mm.

A dielectric layer 35 (which corresponds to dielectric material) is provided on an outer surface of the inner tubular metal layer 33, to form a tube around the inner tubular metal layer 33. In this embodiment, the dielectric layer 35 comprises PTFE and has a thickness of 0.4 mm.

An outer metal layer 37 (which corresponds to an outer conductive layer) is provided on a surface of the dielectric layer 35. In this embodiment the outer metal layer 37 comprises silver and has a thickness of 0.01 mm.

Of course, in other embodiments the thicknesses of any of the layers may be different to the thicknesses described above, and the material of any of the layers may also be different. For example, the dielectric layer 35 may comprise a different low-loss microwave dielectric material, or a different radiofrequency dielectric material, instead of PTFE, and the inner and/or outer metal layers 33, 37 may be formed of metal(s) other than silver.

The inner metal layer 33, dielectric layer 35 and outer metal layer 37 form a coaxial transmission line for conveying radiofrequency and/or microwave frequency energy to an electrosurgical instrument connected thereto.

In one embodiment, this structure may be manufactured by coating the inner metal layer 33 and the outer metal layer 37 on the inner and outer surfaces of the dielectric layer 35, respectively. Alternatively, the inner metal layer 33 and/or the outer metal layer 37 may comprise solid metal tubes positioned on the inner or outer surface of the dielectric layer 35.

Figure 4:
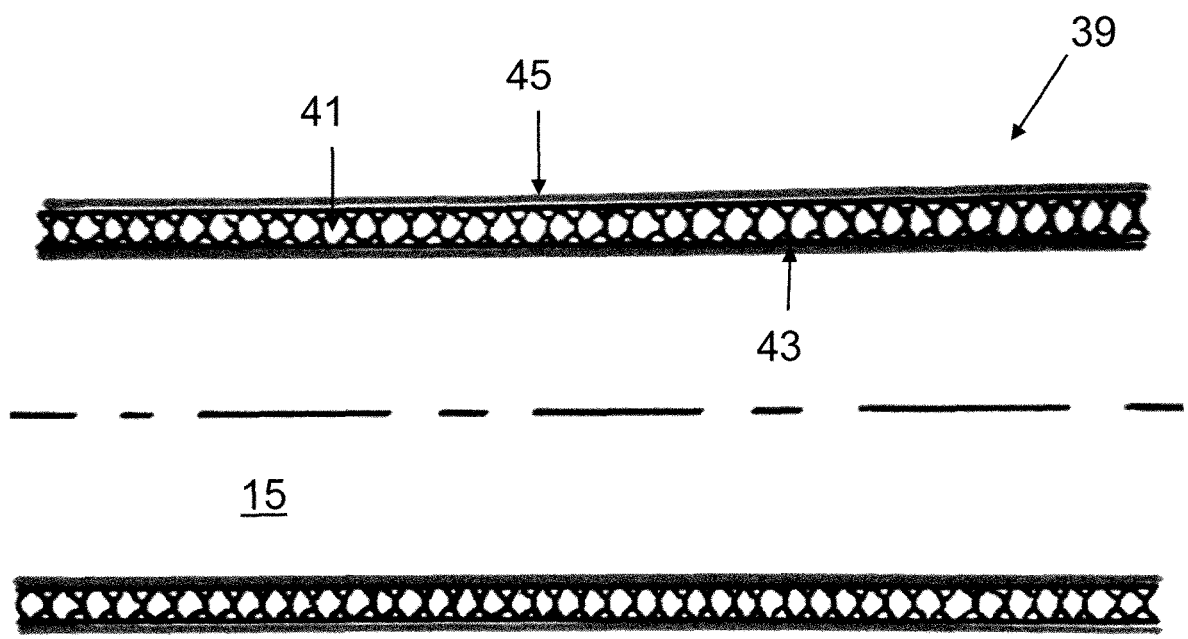
FIG. 4 is a schematic illustration of a part of a cable according to an alternative embodiment of the present invention.

A schematic illustration of a part of a cable according to an alternative embodiment of the present invention is illustrated in FIG. 4. FIG. 4 only shows selected details of the cable relating to its general construction, and does not show the connection to the electrosurgical instrument. The dashed line in FIG. 4 is intended to illustrate a central axis of the cable.

The cable 39 illustrated in FIG. 4 comprises an inhomogeneous porous structure of dielectric material 41. The inhomogeneous porous structure may be, for example, a honeycomb structure, a mesh structure, or a foam structure formed from a foam material. The dielectric material 41 may comprise PTFE.

An inner metal layer 43 is provided on an inner surface of the dielectric material 41 and an outer metal layer 45 is provided on an outer surface of the dielectric material 41.

The inner metal layer 43, dielectric layer 41 and outer metal layer 45 form a coaxial transmission line for conveying radiofrequency and/or microwave frequency energy to an electrosurgical instrument connected thereto.

The inhomogeneous porous structure of the dielectric material 41 may improve the microwave dielectric properties of the dielectric material 41. In other words, the dielectric material 41 may be a more effective low-loss microwave dielectric.

In this embodiment, one or both of the inner metal layer 43 and the outer metal layer 45 may be a solid metal tube, rather than a metal coating. This may improve the mechanical strength and structural integrity of the cable.

Alternatively, one or both of the inner metal layer 43 and the outer metal layer 45 may be a metal coating and may be formed on an additional tubular layer provided on the inner surface of the inner metal layer 43 or on the outer surface of the outer metal layer 45, to provide mechanical support for the cable. Such an additional tubular layer may be formed of PTFE or Polyimide, for example.

Figure 5:
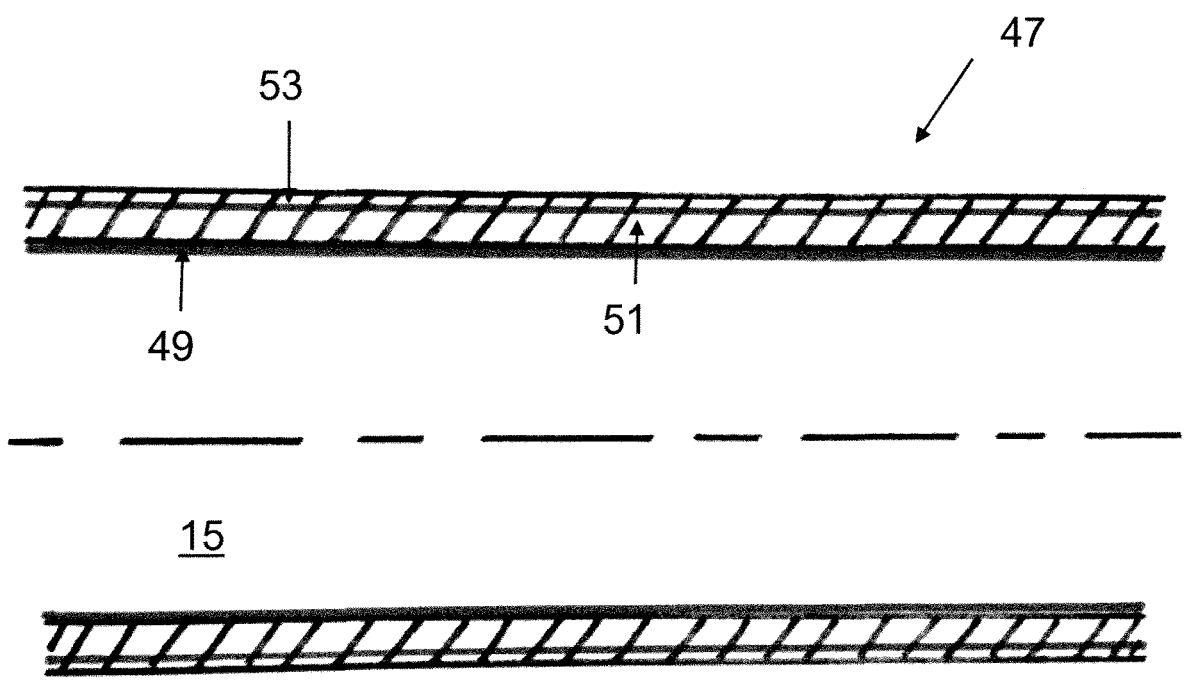
FIG. 5 is a schematic illustration of a part of a cable according to an alternative embodiment of the present invention.

A schematic illustration of a part of a cable according to an alternative embodiment of the present invention is illustrated in FIG. 5. FIG. 5 only shows selected details of the cable relating to its general construction, and does not show the connection to the electrosurgical instrument. The dashed line in FIG. 5 is intended to illustrate a central axis of the cable.

The cable 47 illustrated in FIG. 5 comprises an inner metal layer 49 and a dielectric layer 51 provided on an outer surface of the inner metal layer 49. The cable further comprises a braided metal structure 53 (which corresponds to the outer conductive layer) embedded in the dielectric layer 51.

In one embodiment, this construction may be manufactured by extruding or otherwise forming part of the dielectric layer 51 on a surface of the inner metal layer 49, braiding the braided metal structure 53 over the part of the dielectric layer 51, and then extruding or otherwise forming the remainder of the dielectric layer 51 over the braided metal structure 53.

In an alternative embodiment, the material coated on top of the braided metal structure 53 may be different from the material below (inside) the braided metal structure 53. For example, the braided metal structure 53 may be formed over a dielectric layer 51, and then a different material may be extruded or otherwise formed over the braided metal structure 53. This different material may not be a dielectric material and may instead be an insulating material such as Polyimide.

The inner metal layer 49 may comprise a solid tube of metal, or alternatively may be a metal coating, for example a silver coating, formed on an outer surface of a further tubular layer (not shown), such as a tubular layer of PTFE or Polyimide.

In this embodiment, the braided metal structure is formed by braiding copper or steel wire coated with silver. Of course, other metals may be used in other embodiments.

In this embodiment, the dielectric material comprises PTFE.

Any of the configurations disclosed above may be used in the present invention. Variations of the described embodiments may also be used. For example, in the embodiments a metal coating on the surface of a tube of material may be replaced with a solid metal tube instead, and vice versa.

In some embodiments of the present invention, the outer diameter of the cable may be reduced for part of its length near, or at, the end of the cable where the cable is attached to the electrosurgical instrument. This may facilitate connection of the cable to the electrosurgical instrument.

Figure 6:
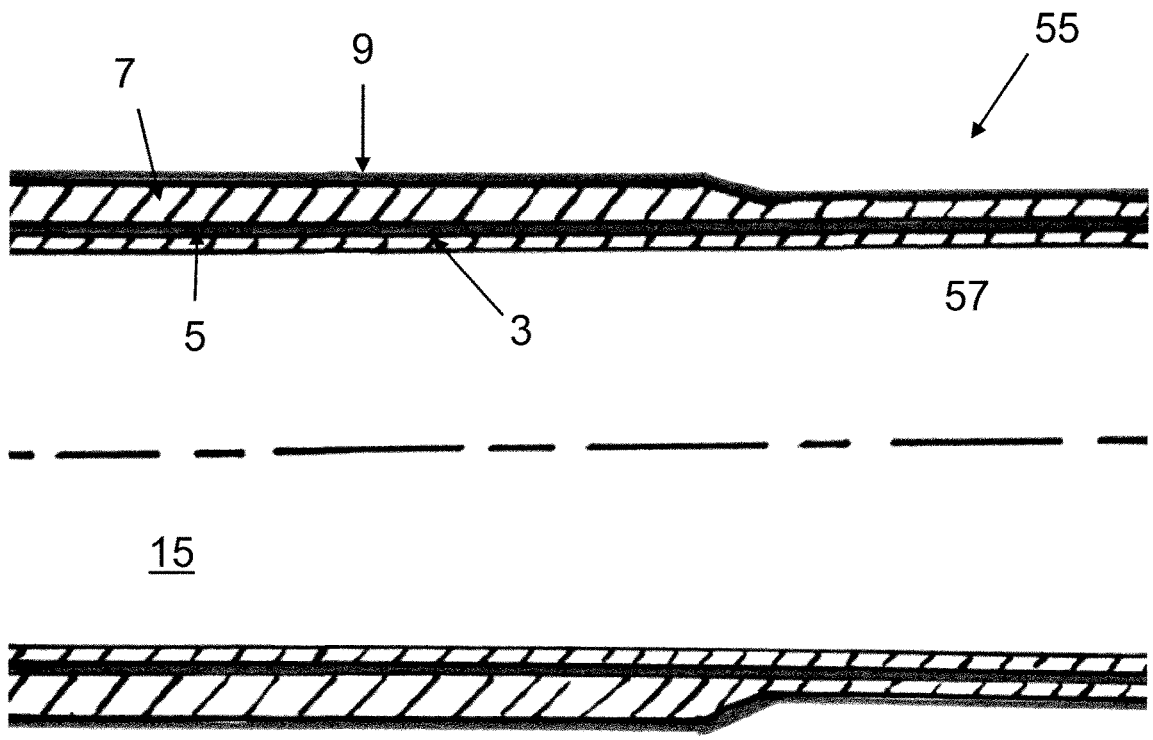
FIG. 6 is a schematic illustration of a part of a cable according to an alternative embodiment of the present invention in which an outer diameter of the cable is narrower near an end thereof.

As an example, this is illustrated in FIG. 6 for a cable with the configuration illustrated in FIG. 1. In the cable 55 illustrated in FIG. 6, the thickness of the dielectric layer 7 is reduced over a part 57 of the length of the cable 55 adjacent to the end of the cable 55. For example, the thickness of the dielectric layer 7 may be reduced from 0.4 mm to a thickness of 0.2 mm or 0.1 mm in the reduced thickness part, so that the overall diameter of the cable 55 is reduced by 0.4 mm or 0.6 mm without changing the internal diameter of the cable 55. Although not shown, the edge of the dielectric layer 7 may still be set back as illustrated in FIG. 1. In one embodiment, the thickness of the dielectric layer 7 may be reduced over a length of 20 mm adjacent to the end of the cable. The reduction in thickness may be achieved by machining down the dielectric layer 7, for example. The length of the portion of the cable having the reduced thickness may be 20 mm, for example. The maximum length of the reduced thickness portion that can be used in practice (in terms of acceptable power losses in the cable) depends on the specific thickness of the dielectric material and the electrical properties of the dielectric material. This may be determined for a particular configuration by simulation and/or measurement.

The same effect may be achieved in the other embodiments by reducing the thickness of one or more of the dielectric material and the other tubular layer if present so as to reduce the outer diameter of the cable at the end of the cable where the electrosurgical instrument is connected.

Alternatively, or in addition, the outer diameter of the cable may be reduced in the part near the end where it is connected to the electrosurgical device by reducing an internal diameter of the cable.

Figure 7:
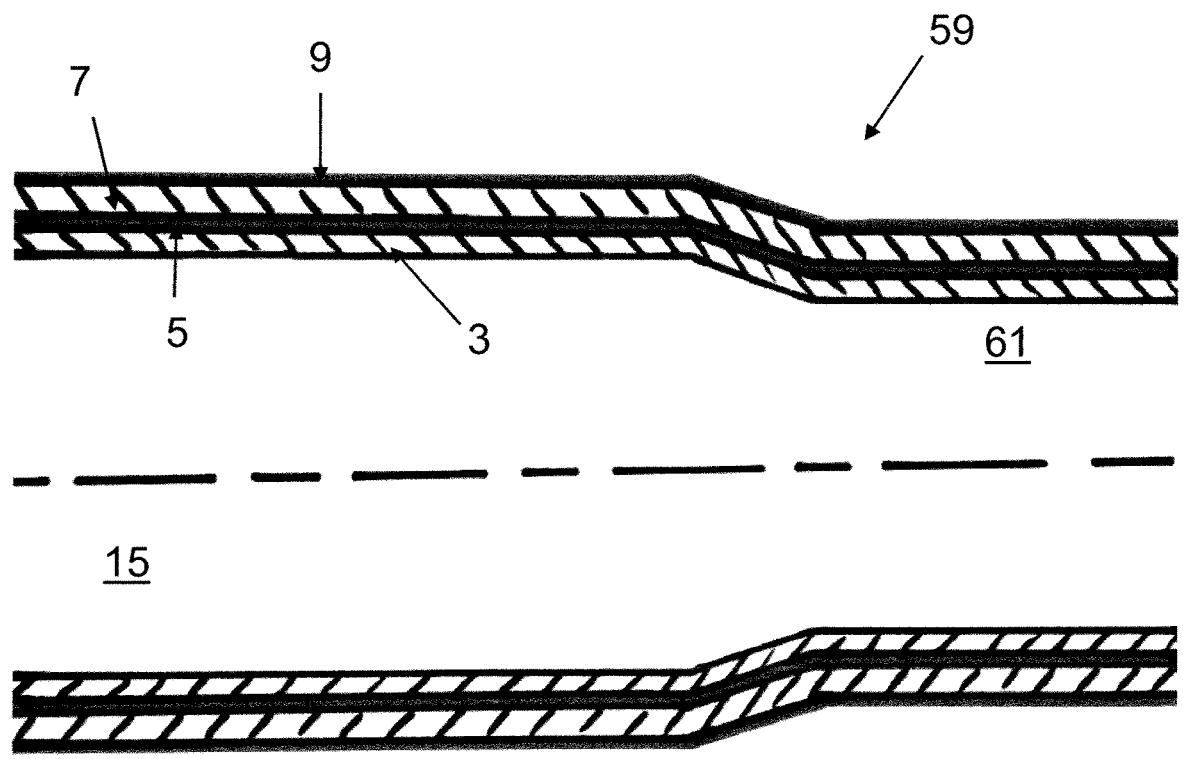
FIG. 7 is a schematic illustration of a part of a cable according to an alternative embodiment of the present invention in which in which an outer and an inner diameter of the cable are narrower near an end thereof.

As an example, this is illustrated in FIG. 7 for a cable with the configuration illustrated in FIG. 1. In the cable 59 illustrated in FIG. 7, the internal diameter of the cable is reduced over a part 61 of the length of the cable 59 by deflecting or moving the outer wall of the cable 59 inwards in the part 61 so that an inner diameter of the cable 59 is reduced. The length of the cable having the reduced thickness may be 20 mm, for example.

The same effect can be achieved with the other embodiments described above by moving the wall of the cable inwards to reduce an inner diameter of the cable.

In any of the described embodiments, if the cable is for conveying radiofrequency energy only the dielectric material may be a suitable radiofrequency dielectric material, such as Kapton, or Kapton Polyimide, i.e. a dielectric material with a breakdown strength that is sufficiently greater than the voltage of the radiofrequency energy.

In some embodiments of the present invention, both radiofrequency energy and microwave frequency energy are conveyed using the inner and outer metal layers. However, there may be a risk in some cases of the higher voltage radiofrequency signals causing electrical breakdown of the dielectric material. Thus, in some embodiments of the present invention, radiofrequency signals may be conveyed to the electrosurgical instrument separately from the microwave frequency signals. This may be achieved by conveying the radiofrequency energy using the inner metal layer and/or the outer metal conductor and a conductor positioned in, and extending along, the hollow bore in the cable.

Figure 8:
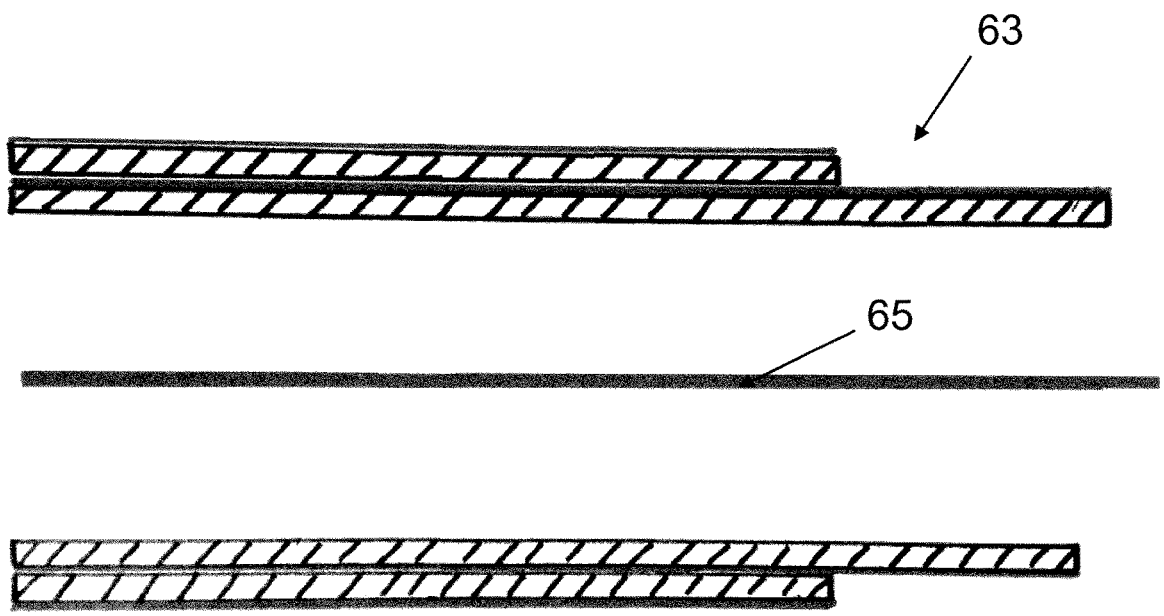
FIG. 8 is a schematic illustration of a cable according to an embodiment of the present invention in which radiofrequency energy is conveyed using a conductor inside the hollow cable.

This is illustrated in FIG. 8 for a cable with the configuration illustrated in FIG. 1. However, the same concept also applies to the other configurations described above, i.e. a conductor may be positioned in the hollow core of the other configurations and used to convey radiofrequency energy. In the cable 63 illustrated in FIG. 8, a conductor 65 is positioned in the hollow core of the cable 63 and extends along the cable 63 to the electrosurgical instrument (not shown). In some embodiments, the conductor 65 may be a metal rod or tube provided for this purpose. However, in other embodiments the conductor 65 may be a conductive outer surface of a part of the electrosurgical instrument, or of a component such as a tube for supplying liquid or gas, or a housing for a guide- or pull-wire or other control means.

The conductor 65 is insulated from the inner and outer metal layers of the cable by the inner tubular layer. For example, the inner tubular layer may comprise an insulating material.

The cable 63 can be connected to a generator configured to supply a radiofrequency signal to the cable through the conductor 65 and the inner metal layer and/or the outer metal layer and a microwave frequency signal through the inner metal layer and the outer metal layer. Thus, the dielectric material may not experience sufficient voltage to cause it to electrically break down, because it may only be exposed to lower voltage microwave frequency signals.

The inner metal layer and the outer metal layer may be electrically connected together at a second (proximal) end of the cable when both the inner and outer metal layers are used to convey the radiofrequency energy together with the central conductor 65.

With this arrangement, it may be necessary to provide one or more components at the end of the cable where it connects to the electrosurgical instrument to prevent the radiofrequency signal from being able to travel back along the microwave transmission path of the inner and outer metal layers, and/or to prevent the microwave signals from travelling back along the conductor 65. Otherwise, the dielectric material may still be exposed to high voltage signals and may still be at risk of break down.

Alternatively, or additionally, in one embodiment the cable may be configured so that the conductor 65 can be pulled axially back along the cable to break the electrical connection between the conductor 65 and the electrosurgical instrument when only microwave frequency energy is being conveyed to the electrosurgical instrument, to prevent microwave frequency energy from travelling along conductor 65.

In order to reduce the risk of electrical breakdown of the dielectric or air gaps occurring in any of the above described embodiments a low-loss fluid or grease or other material may be provided around one or more parts of the cable, for example at likely breakdown areas such as at the ends of one or more of the layers, to reduce the risk of electrical breakdown occurring.

Figure 9:
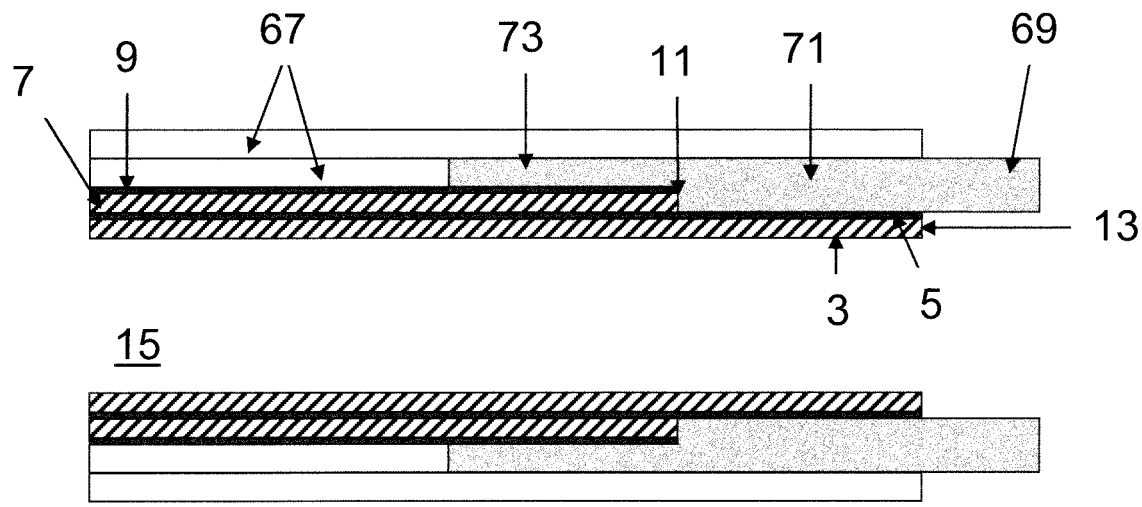
FIG. 9 shows a first configuration according to an embodiment of the present invention for connecting an electrosurgical instrument to a cable so that the electrosurgical instrument is rotatable relative to the cable.

FIG. 9 shows a first configuration according to an embodiment of the present invention for connecting an electrosurgical instrument to a cable so that the electrosurgical instrument is rotatable relative to the cable. The cable illustrated in FIG. 9 has a configuration based on that illustrated in FIG. 1 (although the materials and/or thicknesses of the various layers may be different). The cable further comprises a protective sheath, or covering or coating, 67 provided on an outer surface of the outer metal layer 9 to protect the outer metal layer 9 and to electrically insulate the outer metal layer 9.

An electrosurgical instrument can be connected to the cable so that it can rotate relative to the cable using a rotator spindle 69. The rotator spindle 69 comprises a first portion 71 with a smaller internal diameter and a second portion 73 with a larger internal diameter. In this embodiment, the first and second portions 71, 73 have the same external diameter, but this is not essential. The rotator spindle 69 may comprise a length of tube (a part or short piece of tube). However, as discussed below, in other embodiments the rotator spindle 69 may not comprise a length of tube.

The rotator spindle 69 is positioned around an outside of the first end of the cable.

The rotator spindle 69 is positioned on the first end of the cable so that an inner surface of the first portion 71 faces the inner metal layer 5 exposed in the region between the edge 11 of the dielectric layer 7 (and the outer metal layer 9) and the edge 13 of the inner tubular layer 3 (and the inner metal layer 5). The inner surface of the first portion 71 is configured so that at least a part of the inner surface of the first portion 71 contacts the inner metal layer 5 so that an electrical connection is made between at least a part of the inner surface of the first portion 71 and the inner metal layer 5, and so that the inner surface of the first portion 71 can rotate (for example slide) relative to the inner metal layer 5 while still maintaining the electrical connection.

For example, this may be achieved by the inner surface of the first portion 71 having an internal diameter that corresponds to (i.e. is the same as or slightly larger than) an outer diameter of the inner metal layer 5 and by the inner surface of the first portion 71 being partly or entirely coated in conductive material. Alternatively, this may be achieved by the inner surface of the first portion 71 having a diameter larger than an outer diameter of the inner metal layer 5 and comprising one or more conductive elements biased into contact with the inner metal layer 5, such as a sprung pad, sprung wing, sprung flap or sprung protrusion, so that the one or more conductive elements form a sprung electrical connection to the inner metal layer 5 and can maintain this electrical connection while sliding/rotating.

Furthermore, the rotator spindle 69 is positioned on the first end of the cable so that an inner surface of the second portion 73 faces the outer metal layer 9. The inner surface of the second portion 73 is configured so that at least a part of the inner surface of the second portion 73 contacts the outer metal layer 9 so that an electrical connection is made between at least a part of the inner surface of the second portion 73 and the outer metal layer 9, and so that the inner surface of the second portion 73 can rotate (for example slide) relative to the outer metal layer 9 while still maintaining the electrical connection.

For example, this may be achieved by the inner surface of the second portion 73 having a diameter that corresponds to (i.e. is the same as or slightly larger than) an external diameter of the outer metal layer 9 and by the inner surface of the second portion 73 being partly or entirely coated in conductive material. Alternatively, this may be achieved by the inner surface of the second portion 73 having a diameter larger than an outer diameter of the outer metal layer 9 and comprising one or more conductive elements biased into contact with the outer metal layer 9, such as a sprung pad, sprung wing, sprung flap or sprung protrusion, so that the one or more conductive elements form a sprung electrical connection to the outer metal layer 9 and can maintain this electrical connection while sliding/rotating.

Figure 10:
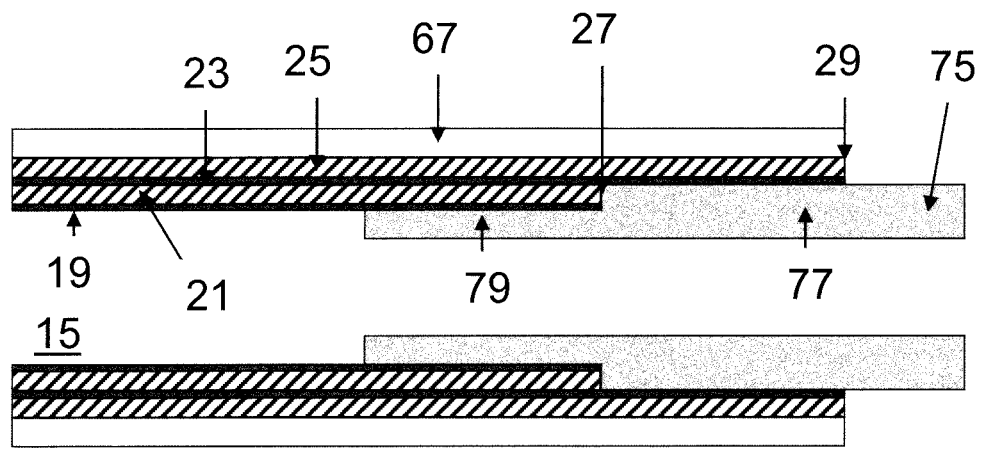
FIG. 10 shows a second configuration according to an embodiment of the present invention for connecting an electrosurgical instrument to a cable so that the electrosurgical instrument is rotatable relative to the cable.

FIG. 10 shows a second configuration according to an embodiment of the present invention for connecting an electrosurgical instrument to a cable so that the electrosurgical instrument is rotatable relative to the cable. The cable illustrated in FIG. 10 has a configuration based on that illustrated in FIG. 2 (although the materials and or thicknesses of the layer may be different). The cable further comprises a protective sheath, or covering or coating, 67 provided on an outer surface of the outer tubular layer 25 to protect the outer tubular layer 25.

An electrosurgical instrument can be connected to the cable so that it can rotate relative to the cable using a rotator spindle 75. The rotator spindle 75 comprises a first portion 77 with a larger outer diameter and a second portion 79 with a smaller outer diameter. In this embodiment the first and second portions 77, 79 have the same inner diameter, but this is not essential. The rotator spindle 75 may comprise a length of tube (a part or short piece of tube), but as described below this may not be the case in some embodiments.

The rotator spindle 75 is positioned on the first end of the cable with the rotator spindle 75 substantially received inside the cable.

The rotator spindle 75 is positioned on the first end of the cable so that an outer surface of the first portion 77 faces the outer metal layer 23 exposed in the region between the edge 29 of the outer metal layer 23 (and the outer tubular layer 25) and the edge 27 of the dielectric layer 21 (and the inner metal layer 19). The outer surface of the first portion 77 is configured so that at least a part of the outer surface of the first portion 77 contacts the outer metal layer 23 so that an electrical connection is made between at least a part of the outer surface of the first portion 77 and the outer metal layer 23, and so that the outer surface of the first portion 77 can rotate (for example slide) relative to the outer metal layer 23 while still maintaining the electrical connection.

For example, this may be achieved by the outer surface of the first portion 77 having a diameter that corresponds to (i.e. is the same as or slightly smaller than) an internal diameter of the outer metal layer 23 and by the outer surface of the first portion 77 being partly or entirely coated in conductive material. Alternatively, this may be achieved by the outer surface of the first portion 77 having a diameter smaller than an internal diameter of the outer metal layer 23 and comprising one or more conductive elements biased into contact with the outer metal layer 23, such as a sprung pad, sprung wing, sprung flap or sprung protrusion, so that the one or more conductive elements form a sprung electrical connection to the outer metal layer 23 and can maintain this electrical connection while sliding/rotating.

Furthermore, the rotator spindle 75 is positioned on the first end of the cable so that an outer surface of the second portion 79 faces the inner metal layer 19. The outer surface of the second portion 79 is configured so that at least a part of the outer surface of the second portion 79 contacts the inner metal layer 19 so that an electrical connection is made between at least a part of the outer surface of the second portion 79 and the inner metal layer 19, and so that the outer surface of the second portion 79 can rotate (for example slide) relative to the inner metal layer 19 while maintaining the electrical connection.

For example, this may be achieved by the outer surface of the second portion 79 having a diameter that corresponds to (i.e. is the same as or slightly smaller than) an internal diameter of the inner metal layer 19 and by the outer surface of the second portion 79 being partly or entirely coated in conductive material. Alternatively, this may be achieved by the outer surface of the second portion 79 having a diameter smaller than an inner diameter of the inner metal layer 19 and comprising one or more conductive elements biased into contact with the inner metal layer 19, such as a sprung pad, sprung wing, sprung flap or sprung protrusion, so that the one or more conductive elements form a sprung electrical connection to the inner metal layer 19 and maintain this electrical connection while sliding/rotating.

Figure 11:
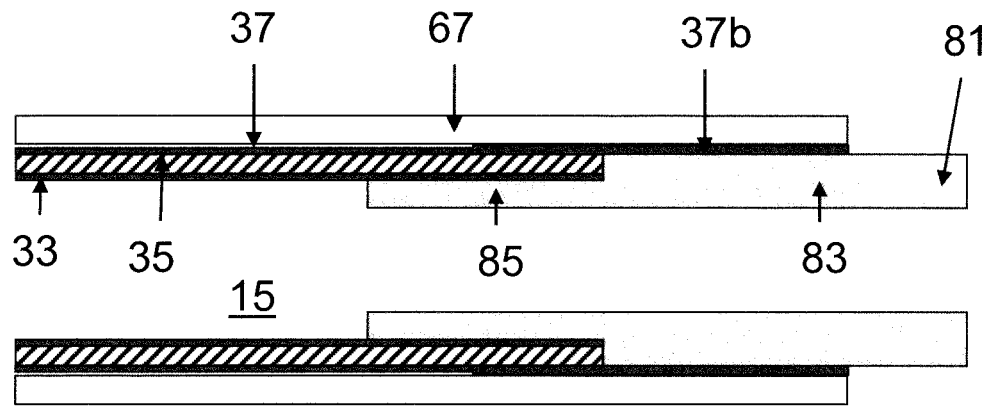
FIG. 11 shows a third configuration according to an embodiment of the present invention for connecting an electrosurgical instrument to a cable so that the electrosurgical instrument is rotatable relative to the cable.

FIG. 11 shows a third configuration according to an embodiment of the present invention for connecting an electrosurgical instrument to a cable so that the electrosurgical instrument is rotatable relative to the cable. The cable illustrated in FIG. 11 has a configuration based on that illustrated in FIG. 3 (although the materials and or thicknesses of the layer may be different). The cable further comprises a protective sheath, or covering or coating, 67 provided on an outer surface of the In addition, in the configuration illustrated in FIG. 11 the outer metal layer 37 comprises a portion 37b that extends beyond an edge of the dielectric material 35 so that it is exposed on an inner circumferential surface of the cable. For example, the portion 37b may comprise a hollow solid metal tube or cylinder. Where the outer metal layer 37 is a hollow solid metal tube or cylinder, the portion 37b may be an integral extension of the outer metal layer 37. Alternatively, where the outer metal layer 37 is a metal coating, the portion 37b may be a separate conductive portion that is electrically connected to the outer metal layer 37, e.g. by being in physical contact with the outer metal layer 37. In one embodiment, the portion 37b may be provided (for example coated) on an inner surface of the protective sheath 67.

An electrosurgical instrument can be connected to the cable so that it can rotate relative to the cable using a rotator spindle 81. The rotator spindle 81 comprises a first portion 83 with a larger outer diameter and a second portion 85 with a smaller outer diameter. In this embodiment the first and second portions 83, 85 have the same inner diameter, but this is not essential. The rotator spindle 81 may comprise a length of tube (a part or short piece of tube), but as discussed below in some embodiments this may not be the case.

The rotator spindle 81 is positioned on the first end of the cable with the rotator spindle 81 substantially received inside the cable.

The rotator spindle 81 is positioned on the first end of the cable so that an outer surface of the first portion 83 faces the portion 37b of the outer metal layer 37. The outer surface of the first portion 83 is configured so that at least a part of the outer surface of the first portion 83 contacts the portion 37b so that an electrical connection is made between at least a part of the outer surface of the first portion 83 and the portion 37b, and so that the outer surface of the first portion 83 can rotate (for example slide) relative to the portion 37b while maintaining the electrical connection.

For example, this may be achieved by the outer surface of the first portion 83 having a diameter that corresponds to (i.e. is the same as or slightly smaller than) an internal diameter of the portion 37b and by the outer surface of the first portion being partly or entirely coated with conductive material. Alternatively, this may be achieved by the outer surface of the first portion 83 having a diameter smaller than an internal diameter of the portion 37b and comprising one or more conductive elements biased into contact with the portion 37b, such as a sprung pad, sprung wing, sprung flap or sprung protrusion, so that the one or more conductive elements form a sprung electrical connection to the portion 37b and maintain this electrical connection while sliding/rotating.

Furthermore, the rotator spindle 81 is positioned on the first end of the cable so that an outer surface of the second portion 85 faces the inner metal layer 33. The outer surface of the second portion 85 is configured so that at least a part of the outer surface of the second portion 85 contacts the inner metal layer 33 so that an electrical connection is made between at least a part of the outer surface of the second portion 85 and the inner metal layer 33, and so that the outer surface of the second portion 85 can rotate (for example slide) relative to the outer metal layer 33 and can maintain the electrical connection while rotating.

For example, this may be achieved by the outer surface of the second portion 85 having a diameter that corresponds to (i.e. is the same as or slightly smaller than) an internal diameter of the inner metal layer 33 and by the outer surface of the second portion 85 being partly or entirely coated with conductive material. Alternatively, this may be achieved by the outer surface of the second portion 85 having a diameter smaller than an internal diameter of the inner metal layer 33 and comprising one or more conductive elements biased into contact with the inner metal layer 33, such as a sprung pad, sprung wing, sprung flap or sprung protrusion.

In any of the above described configurations, the rotator spindle may be an integral part of the electrosurgical instrument. Alternatively, the rotator spindle may be connected to the electrosurgical instrument (electrically and mechanically). For example, the rotator spindle and the electrosurgical instrument may comprise one or more corresponding protrusions and/or recesses for connecting the electrosurgical instrument to the rotator spindle. Alternatively, the electrosurgical instrument may be connected to the rotator spindle by fixing one or more parts of the electrosurgical instrument to the rotator spindle, for example through welding or through an adhesive or bonding material. Alternatively, or in addition, the rotator spindle may have electrical connection terminals for being electrically connected to corresponding terminals of the electrosurgical instrument, for providing a bipolar electrical connection between the rotator spindle and the electrosurgical instrument. Thus, the electrosurgical instrument may be rotatable relative to the cable by rotating the electrosurgical instrument and the integral or connected rotator spindle relative to the cable.

In any of the configurations described above, electrical connection between a portion of the rotator spindle and a corresponding metal layer may be made at a plurality of different locations on the portion of the rotator spindle, for example by physical contact occurring between the portion of the rotator spindle and the corresponding metal layer at the plurality of different locations. An advantage of making the electrical connection at a plurality of locations is that the capacitance will be reduced relative to an arrangement with an electrical connection at only one location, for example.

In addition, or alternatively, a conductive grease may be present between any gaps between the portion of the rotator spindle and the corresponding metal layer, to provide a more uniform electrical connection between the portion of the rotator spindle and the corresponding metal layer.

The rotator spindle may comprise an insulating material that is selectively coated with conductive material for forming the sliding electrical connections with the inner and outer metal layers. For example, portions of the rotator spindle may be selectively coated with one or more circumferential bands and/or axial strips of conductive material on the inner or outer surface for forming a sliding electrical connection with a corresponding metal layer.

Where the rotator spindle comprises a length of tube, electrical connections to the metal layers may be achieved by providing a circumferential ring or band of conductive material around the inner or outer surface of the portion of the rotator spindle (depending on the particular configuration of the cable). These conductive bands may then be electrically connected to terminals on an end face of the rotator for electrically connecting to an electrosurgical instrument by paths of conductive material positioned on the inside or outside surfaces of the rotator spindle.

The rotator spindle may comprise an insulating material that is selectively coated with conducting material to leave appropriate connection terminals for connection to the electrosurgical instrument.

Selective coating of the rotator spindle with conductive material may be achieved by first applying a uniform coating and then by removing, for example by etching, appropriate areas of material.

In all of the above described embodiments, the rotator spindle comprises a longitudinal passageway (a central closed channel or bore in these embodiments) that is continuous with a central passageway of the hollow tube of the cable.

In some embodiments, the first portion and/or the second portion of the rotator spindle (i.e. the portions having different internal or external diameters) may be lengths of a hollow tube (or pipe). In other words, an outer surface of the portion may span an angle of 360 degrees around a central axis of the portion to form a closed loop (or circle) around the central axis.

However, in other embodiments the first portion and/or the second portion of the rotator spindle may comprise lengths of a hollow tube (or pipe) in which portions of the hollow tube have been omitted or removed, so that an outer surface of the portion spans an angle of less than 360 degrees around a central axis of the portion and does not form a closed loop.

Figure 12A:
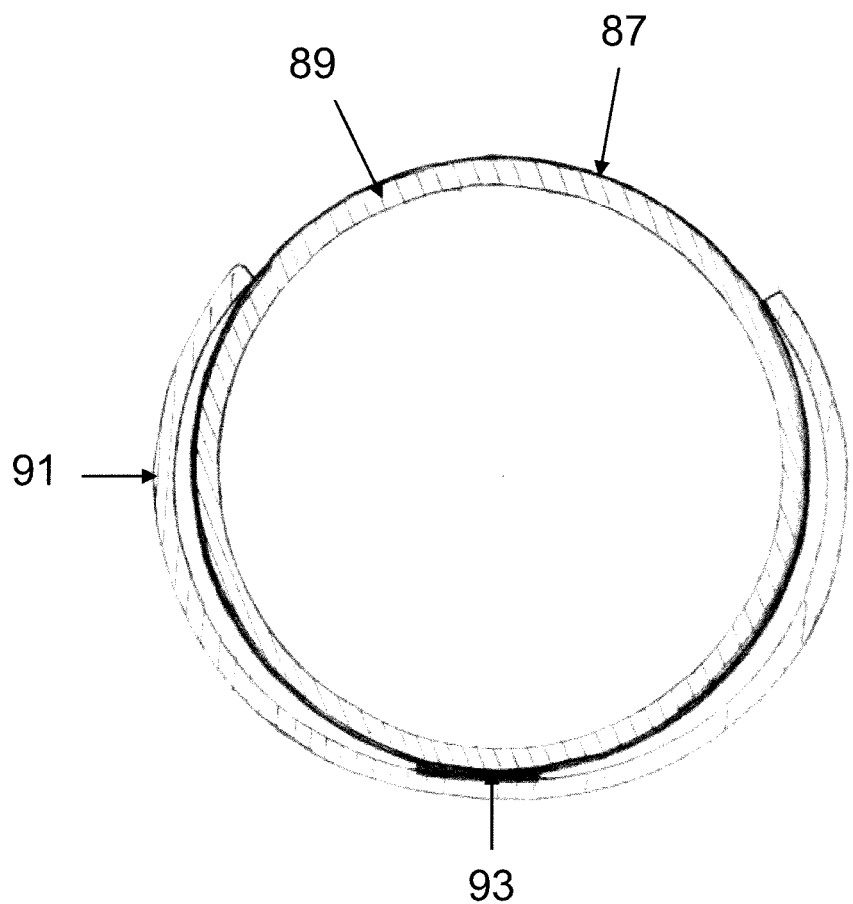

For example, FIG. 12A illustrates the basic concept of forming a rotating electrical connection to a tubular metal layer using a tube (or pipe) from which a portion has been removed or omitted (for example cut, e.g. by laser cutting). Of course, in other embodiments a first portion having a configuration based on that illustrated in FIG. 12A may be made in a way other than removing a portion of an existing tube. For example, a first portion having a configuration based on that illustrated in FIG. 12A may be made by moulding or otherwise forming the shape of the first portion, rather than forming a tube and then removing part(s) of it.

In FIG. 12A, a metal layer 87 is provided on an outer surface of a hollow tube of material 89. For example, the tube of material 89 could be the inner tubular layer 3 and the metal layer 87 could be the inner metal layer 5 of FIGS. 1 and 9, or the tube of material 89 could be the dielectric material 7 and the metal layer 87 could be the outer metal layer 9 of FIGS. 1 and 9.

In FIG. 12A, a rotating electrical connection is made to the metal layer 87 using a partial tube 91 (a tube from which an axial strip has been removed or omitted from the circumference of the tube so that the outer circumference of the tube does not form a closed loop around the central axis of the tube). In this embodiment, the partial tube 91 comprises a tube with a similar (i.e. the same or smaller) initial diameter to the outer surface of the metal layer 87 from which an axial strip has been cut out of the circumference so that the outer surface of the partial tube no longer forms a closed loop (or circle) around a central axis of the partial tube 91. In FIG. 12A the partial tube 91 has been stretched to fit around the outer surface of the metal layer 87 to provide a sprung secure and rotating connection between the partial tube 91 and the metal layer 87. The partial tube 91 presses inwards on the metal layer 87 in a plurality of locations, for example in a central region of the partial tube 91 and at the edges of the partial tube 91 that extend in the axial direction.

The sides of the partial tube 91 can be considered to be sprung wings that grip an outer surface of the metal layer.

The partial tube 91 may be formed form a naturally sprung material, for example Polyimide.

The partial tube 91 comprises a conductive strip 93 on the inner surface thereof that extends axially along the partial tube 91. The conductive strip 93 is positioned at a central position of the partial tube 91, where the partial tube 91 contacts the metal layer 87. Therefore, a secure electrical connection is formed between the conductive strip 93 and the metal layer 87 at all times as the partial tube 91 rotates relative to the metal layer 87.

FIG. 12B is a schematic illustration of the partial tube 91 positioned around the inner metal layer 5 of the cable configuration illustrated in FIG. 1. FIG. 12C is a schematic illustration of the inner surface of the partial tube 91 showing the conductive strip 93 on the inner surface.

FIGS. 12A to 12C only show a rotatable electrical connection being formed to a single metal layer. Of course, in embodiments of the present invention two such partial tubes 91a, 91b may be provided for forming rotatable electrical connections to the inner and outer metal layers of the cable. For example, in FIG. 12B a second partial tube 91b with a larger diameter than the first partial tube 91a could be positioned around the outer metal layer 9 for forming a rotatable electrical connection to the outer metal layer 9. The two partial tubes may be integrally formed, or may be mechanically connected or attached together.

FIGS. 12D and 12E illustrate an example of a rotator spindle that comprises a first partial tube 91a for forming a rotatable electrical connection to an inner metal layer and a second partial tube 91b for forming a rotatable electrical connection to an outer metal layer. The first and second partial tubes 91a, 91b are integrally formed from the same insulating material (e.g. Polyimide) and are selectively coated with conductive material for forming appropriate electrical connections to the metal layers.

As described above, the partial tubes may be positioned around the outsides of the corresponding metal layers for forming a sprung connection to the metal layers. Alternatively, in other embodiments an equivalent rotatable electrical connection may be made to a metal layer on an inside of a tube of material by providing a partial tube 91 formed from a tube with an initial diameter that is larger than the inner diameter of the metal layer, so that the partial tube 91 is compressed to fit inside the metal layer and presses outwards against the metal layer in a plurality of places. This arrangement is illustrated in FIG. 12F, which shows a partial tube 91 that has been compressed to fit inside a tube so that the wings of the partial tube 91 press outwards against the inside of the tube, thereby forming a sprung connection to the inside of the tube.

The partial tubes illustrated in FIGS. 12A to 12E all have longitudinal passageways, in the form of open channels that are bounded on only some of the circumference thereof by the walls of the partial tube, that are continuous with a central passageway of the hollow tube of the cable.

Figure 13:
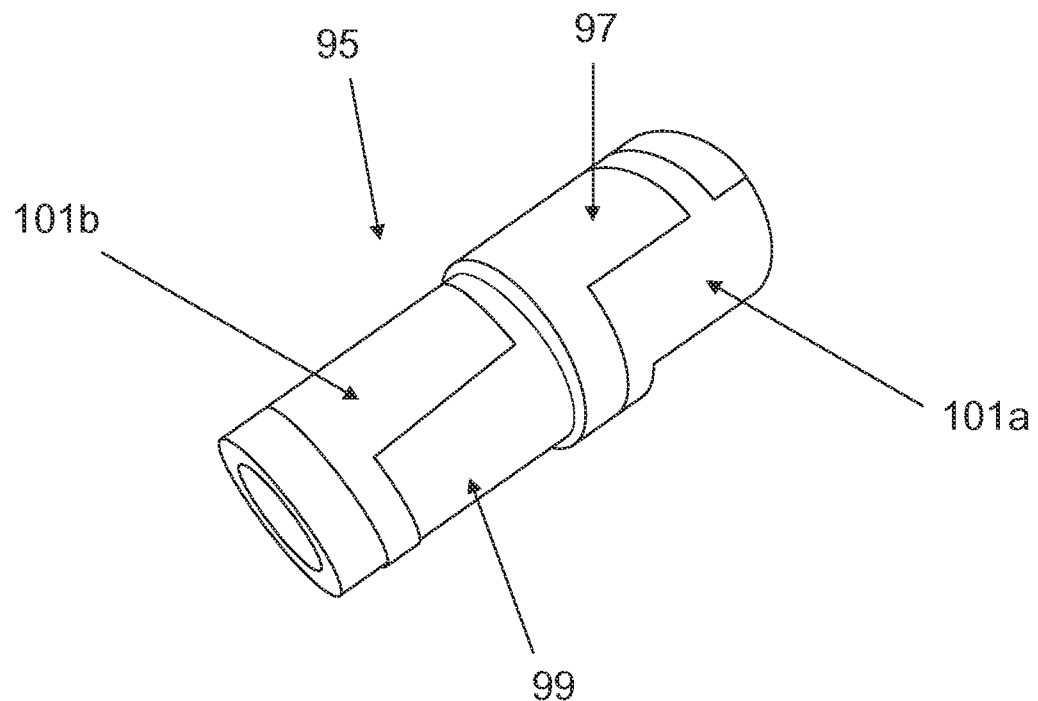
FIG. 13 is a schematic illustration of a rotator spindle according to an embodiment of the present invention for providing relative rotation between an electrosurgical instrument connected to the rotator spindle and a cable.

FIG. 13 is a schematic illustration of an alternative configuration of a rotator spindle for enabling electrical connection and relative rotation between an electrosurgical instrument connected to (or integral with) the rotator spindle and a cable.

The rotator spindle 95 has a configuration similar to that illustrated in FIGS. 10 and 11. In other words, the rotator spindle 95 comprises a first portion 97 with a larger outer diameter and a second portion 99 with a smaller outer diameter. The rotator spindle 95 is primarily formed from insulating material. For example, it may be manufactured at least in part from moulded plastic. The first portion 97 of the rotator spindle 95 comprises one or more integral spring pads 101a and the second portion 99 comprises one or more integral spring pads 101b. The spring pads 101a, 101b stick out or project from the outer surface of the first portion 97 or the second portion 99 respectively in their natural (or rest) state and can be displaced back towards the respective outer surface against the action of a spring force that acts to return them to their natural (or rest state). The outer surfaces of the spring pads 101a, 101b are coated with a conductive material.

Thus, when the rotator spindle 95 is positioned on an end of the cable with the second portion 99 received inside an inner metal layer and the first portion 97 received inside an outer metal layer, for example as illustrated in FIG. 10 or FIG. 11, the spring pad 101b on the second portion 99 will contact the inner metal layer and will be biased towards the inner metal layer (due to it being pressed backwards and the resulting spring force). A secure and reliable sprung connection will thereby be formed between the rotator spindle 95 and the inner metal layer that enables rotation between the rotator spindle 95 and the inner metal layer and that electrically connects the rotator spindle 95 and the inner metal layer through the conductive material coated on the spring pad 101b. A corresponding connection is formed between the rotator spindle 95 and the outer metal layer through the spring tab 101a of the first portion contacting and being biased towards the outer metal layer.

One or more paths (i.e. lines or portions) of conductive material may be formed on the rotator spindle 95 for electrically connecting the conductive material on the spring pads 101a, 101b to terminals for connecting the rotator spindle to an electrosurgical instrument, which may be located on an end face of the rotator spindle. For example, these paths may pass down the inner or outer circumferential surfaces of the rotator spindle 95.

A corresponding rotator spindle may be used with configurations such as that illustrated in FIG. 9 in which the first and second metal layers are provided on the outer surfaces of tubular layers and the first and second portions of the rotator spindle are positioned on the outer sides of the metals layers. In that case, the spring pads may stick out or project inwardly from the inner surface of the first portion or the second portion respectively in their natural (or rest) state, in order to form a sprung connection between the portion and a respective metal layer positioned inside the portion.

In any of the embodiments described above, the axial position of the rotator spindle may be fixed, to prevent the rotator spindle moving axially (and therefore breaking the electrical connection). This may be achieved in one embodiment by providing one or more projections and/or corresponding protrusions on the rotator spindle and the cable which interact to prevent the rotator spindle from moving axially. In one embodiment, the cable may have one or more apertures that pass through the entire width of the cable, for example laser cut apertures. The rotator spindle may have one or more circumferential channels or recesses in the surface thereof that line up with the one or more apertures when the rotator spindle is in the correct axial position. A stop may be fitted into the one or more apertures so that it protrudes through the aperture and into the corresponding circumferential channel or recess in the rotator spindle. Thus, while the block is in position the rotator spindle can rotate freely because the block is received in the circumferential channel or recess and can move along it during rotation. However, the rotator spindle is prevented from moving axially, because the block abuts an axial wall of the circumferential recess or channel.

An outer protective sheath may be provided over the cable to prevent the blocks from being removed from the apertures during operation of the cable.

In one embodiment, one or more of the blocks may also be used to transfer the electrical signal from the inner metal layer or the outer metal layer to an outside of the cable. Thus, the blocks may perform a dual function, which may reduce the number of components required.

In any of the embodiments described above the cable may narrow at its first end as shown in FIGS. 6 and 7. This may provide more room for connecting a rotating part such as a rotator spindle at the first end of the cable.

Figure 14:
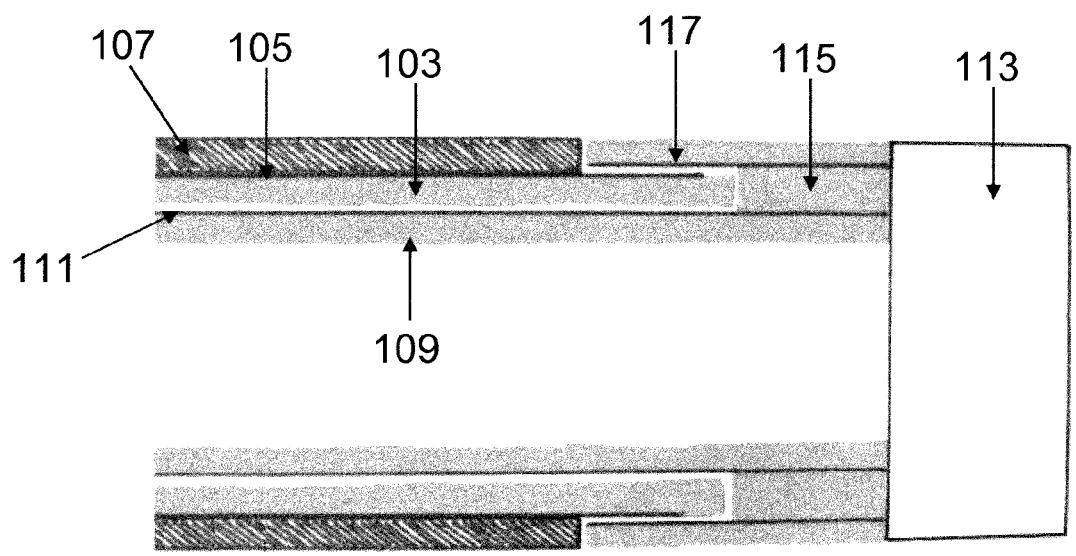
FIG. 14 shows a further configuration of a cable according to an embodiment of the present invention in which the electrosurgical instrument is rotatable relative to the cable.

FIG. 14 shows a further configuration of a cable according to an embodiment of the present invention in which the electrosurgical instrument is rotatable relative to the cable. In the embodiment illustrated in FIG. 14, the cable is split into two primary elements. The first element comprises a layer of dielectric material 103 with an outer metal layer 105 provided (for example coated) on an outer surface thereof and a protective layer 107 provided on an outer surface of the outer metal layer 105.

The second element comprises an inner tubular layer 109 having an inner metal layer 111 provided (for example coated) on the outer side thereof. The inner tubular layer 109 is positioned inside the layer of dielectric material 103 so that the inner metal layer 111 is adjacent to the layer of dielectric material 103. However, the inner metal layer 111 is not attached or connected to the layer of dielectric material 103 and is able to slide relative to the layer of dielectric material so that the second element is rotatable relative to the first element.

The second element further comprises an electrosurgical instrument 113 attached at a first end of the second element. In a region adjacent to the electrosurgical instrument 113, a further layer of dielectric material 115 is provided on the inner metal layer 111, adjacent to an end of the layer of dielectric material 103 and the outer metal layer 105. The further layer of dielectric material 115 has a thickness greater than the combined thickness of the layer of dielectric material 103 and the outer metal layer 105. Furthermore, a further outer metal layer 117 is provided on an outer surface of the further layer of dielectric material 115 so that it extends axially from an edge of the further layer of dielectric material 115 in the opposite direction to the electrosurgical instrument, so as to overlap an exposed portion of the outer metal layer 105. The further outer metal layer 117 contacts the outer metal layer 105 in the region of overlap, thereby forming an electrical connection between the outer metal layer 105 and the further outer metal layer 117. The further outer metal layer 117 can slide relative to the outer metal layer 105, so that the second element is rotatable relative to the first element while still maintaining the electrical connections.

Thus, a connection between the first element and the second element is such the electrosurgical instrument and the second element can be rotated relative to the first element (i.e. the outside of the cable) while maintaining a bipolar electrical connection between to the electrosurgical instrument.

With this configuration, it is possible to both rotate the electrosurgical instrument relative to the cable and also to move the electrosurgical instrument axially relative to the cable. This may allow good control over the orientation and positioning of the electrosurgical instrument.

Some specific example configurations of how to rotate an electrosurgical instrument connected at an end of the cable will now be discussed.

In one embodiment, the electrosurgical instrument may be rotated by connecting an actuator such as a rod, wire, cable or tube to the electrosurgical instrument and by rotating the actuator to directly rotate the electrosurgical instrument. This may provide acceptable rotational control of the electrosurgical instrument in some circumstances. However, the present inventors have realised that in some cases this type of control may lead to rotation of the electrosurgical instrument occurring in a series of jumps (or jolts) or intermittent sudden changes, which may be undesirable in many applications. This is believed to be because of bends in the actuator causing friction and torque pressures.

The present inventors have realised this problem may be overcome by causing rotation of the electrosurgical instrument by pushing or pulling an actuator such as a rod, wire, cable, tube or pipe, to move it axially relative to the electrosurgical instrument, and by providing an interface between the actuator and the electrosurgical instrument that converts this axial movement into a rotational movement of the electrosurgical instrument. The present inventors have realised that axial pulling and pushing movements of an actuator are smoothly transmitted along the cable, even where the cable is bent, so that smooth rotation of the electrosurgical instrument can be achieved.

Figure 15:
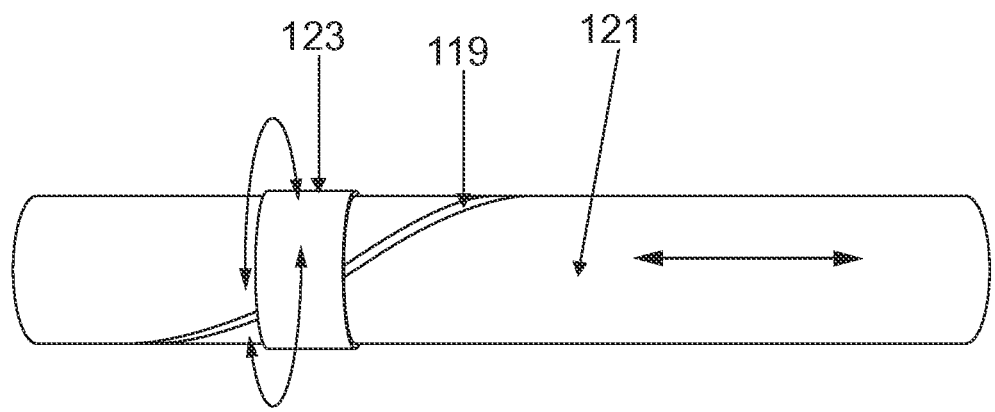
FIG. 15 shows a configuration according to an embodiment of the present invention for converting axial movement of an actuator into rotational movement of the electrosurgical instrument.

In one embodiment, as illustrated in FIG. 15, this is achieved by providing a raised helix 119 on an outer surface of the actuator 121, which in this embodiment is a hollow flexible pipe. A corresponding rotator 123 is provided over the helix 119 that is connected (either directly or indirectly through other parts or components) to the electrosurgical tool. The rotator 123 comprises a hollow tube or pipe. The rotator 123 has some means or structure for causing the rotator 123 to follow the path of the raised helix 119. For example, the rotator 123 may have a curved channel or groove for receiving the raised helix 119. The rotator 123 is prevented from moving axially with the actuator 121 by some means not illustrated in FIG. 15, which is discussed in more detail below. Therefore, as the actuator 121 is moved axially relative to the rotator 123, the rotator 123 is held in the same axial position and is caused to rotate relative to the actuator 121 by the interaction between the raised helix 119 and the rotator 123.

In the embodiment illustrated in FIG. 15 the raised helix 119 comprises a wire bent around the actuator 121 in a helical pattern. However, in other embodiments the raised helix 119 may be configured differently. For example, in one embodiment the raised helix 119 may comprise a tube that is cut (for example laser cut) to produce the helical shape and then attached (for example bonded) onto the outside of the actuator 121. Alternatively, the raised helix 119 may be formed on the outer surface of the actuator 121 by selectively removing material from the outer surface of the actuator 121, for example by laser etching, so that the actuator 121 and raised helix 119 are formed from a single tube.

In this embodiment, the raised helix 119 comprises a single very small low pitch thread. This may enable the rotator 123 to have a good bearing on the actuator 121, giving it a smooth rotation action.

Since the actuator 121 is a hollow pipe in this embodiment, other components such as a liquid or gas feed, or a pull-wire or other actuators can be passed thought the hollow pipe in use of the cable. Thus, the actuation for rotating the electrosurgical instrument does not significantly restrict the provision of other components through the hollow cable.

The rotator 123 illustrated in FIG. 15 may be integral with, or connected to, any of the previously described rotational configurations, such as the rotation spindles illustrated in FIGS. 9 to 13 or the second element illustrated in FIG. 14, thereby enabling the electrosurgical tool to be accurately rotated in any of these embodiments.

In some embodiments, the rotator 123 may be significantly longer in the axial direction than the rotator 123 shown in FIG. 15. This may provide additional space for providing a seal.

In other embodiments, the interaction between the actuator and the rotator to convert linear motion of the actuator into rotation of the rotator may be different to that illustrated in FIG. 15. For example, instead of having a raised helix the actuator may instead have a helical groove or slot on its outer surface, and the rotator may have a follower, for example a protrusion such as a pin, received in the helical groove or slot so that the follower follows the path of the groove or slot. Thus, as the actuator is moved axially and the axial position of the rotator is fixed, the rotator is caused to rotate.

Figure 16:
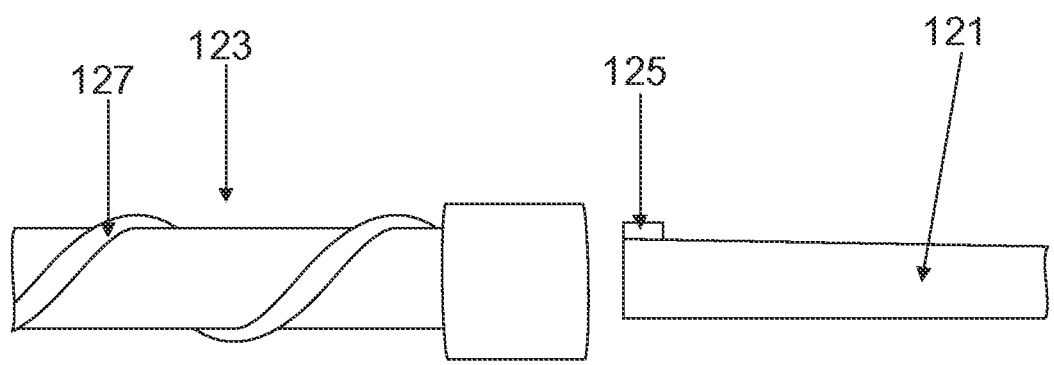
FIG. 16 shows an alternative configuration according to an embodiment of the present invention for converting axial movement of an actuator into rotational movement of the electrosurgical instrument.

In an alternative embodiment, the rotator may instead comprise the helical grove or slot and the actuator may comprise the follower received in the helical groove or slot of the rotator. Thus, as the actuator is moved axially and the rotator is prevented from moving axially, the rotator is caused to rotate. This is illustrated in FIG. 16, in which the actuator 121 comprises a follower 125 and the rotator 123 has a helical groove 127 on its inner surface for receiving the follower 125.

As discussed above, to achieve rotation of the rotator in the above described configurations the rotator is prevented from moving axially. In some embodiments, this may be achieved by providing a stop, such as a ring or protrusion, at the end of the cable for preventing the rotator from being axially displaced further than the stop. In other embodiments, an external cap or sleeve may be fitted over the cable, the cap or sleeve having a stop, such as a ring or protrusion, for preventing the rotator from being axially displaced further than the stop.

In other embodiments, a diameter of the end of the cable may be reduced as illustrated in FIG. 7, and/or by other means such as crimping or heat shrinking to prevent the rotator from escaping from the end of the cable, or by forming a lip or ring at the end of the cable.

In some embodiments, the actuator may further be configured to interact with the cable or with a handle of the cable so that the actuator is prevented from rotating relative to the cable. This may improve the rotation of the rotator and/or make it easier to rotate the rotator. This may be achieved, for example, by providing a linear axial groove or slot in the surface of the actuator in which is received a follower, for example a protrusion such as a pin, on an inner surface of the cable or handle. Alternatively, a linear axial groove or slot may be formed in a surface of the cable or handle in which is received a follower, for example a protrusion or pin, on a surface of the actuator.

In order to impart axial motion to the actuator, a second helical interface may be provided at the proximal end of the cable, whereby rotation of a control knob or the like is transformed into axial movement of the actuator.

In some configurations the rotator spindle described previously and the rotator described previously may be combined (for example attached together) to form a single component.

Figure 17A:
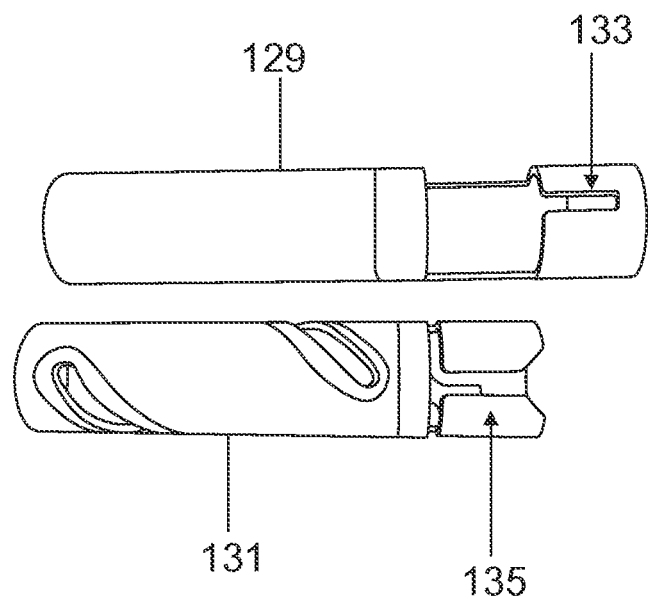
FIGS. 17A to 17C show a configuration for enabling bipolar rotational connection between the cable and an electrosurgical instrument and for converting axial movement of an actuator into rotational movement of the electrosurgical instrument.

FIG. 17A shows an example in which a rotator spindle and a rotator are combined together. The arrangement illustrated in FIG. 17A comprises a first part 129 and a second part 131. The first part 129 comprises a tube of material coated on the outside with conductive material. The first part furthermore comprises a partial tube 133 spaced from an end of the tube of material, for positioning around an outer surface of an outer metal layer of a cable, as discussed previously in relation to the rotator spindle. The partial tube 133 has a conductive coating on the inside thereof for making an electrical connection to the outer metal layer.

The second part 131 comprises a tube of material coated on the outside with conductive material. A helical slot has been cut out of the tube of material, for interacting with a follower on an actuator (not shown). The second part 131 therefore acts as a rotator as described above.

The second part 131 has a partial tube 135 adjacent to the tube of material for positioning around an outer surface of an inner metal layer of a cable, as discussed previously in relation to the rotator spindle.

Figure 17B:
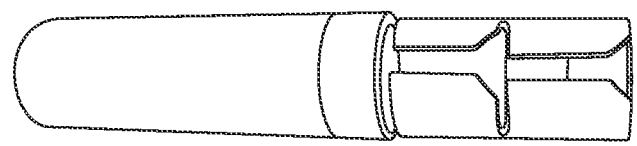

As shown in FIG. 17B, the second part 131 can be slid inside the first part 129 and fixed inside the first part 129 to form a combined rotator spindle and helix (rotator).

Figure 17C:
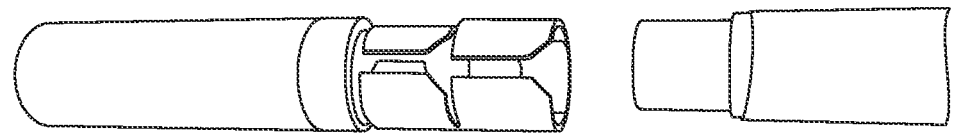

The combined rotator spindle and helix can then be connected to a cable having a configuration corresponding to that illustrated in FIG. 1, as shown in FIG. 17C. Thus, a rotatable bipolar electrical connection is formed between the combined rotator spindle and helix and the cable, and the combined rotator spindle and helix can be made to rotate by axially moving the actuator, which may be an axially sliding sleeve or the like extending through a hollow passage in the cable.

An electrosurgical tool can then be connected to the free end of the combined rotator spindle and helix (left end in FIG. 17C). FIG. 17C does not show the electrical connection interface to the electrosurgical instrument. However, the connection interface may comprise, for example, corresponding conductive recesses and/or protrusions on the cable and on the electrosurgical instrument, such as metal foil tabs, pins or wires and corresponding holes or openings, or corresponding electrical connection terminals on the cable and electrosurgical instrument that are brought into direct physical contact or into electrical contact (for example using wires).

In some cases, it may be necessary to convert a cable having a configuration as illustrated in FIG. 1, in which the metal layers are provided on the outer surfaces of the inner tubular layer and the tube of dielectric material, to a configuration in which the metal layers can be accessed from the insides of these layers. In one embodiment, this may be achieved by providing solid metal tubes of corresponding sizes at the ends of the inner tubular layer and the tube of dielectric material. Conductive foil can be used to mechanically and electrically connect the solid metal tubes to the respective metal layer, allowing the electrical connection to the metal layer to be picked up from the inner surface of the solid metal tube. Thus, a rotator spindle as illustrated in FIG. 10 could be used with a cable having the configuration illustrated in FIG. 1.

The same concept may also be used to convert a cable having a configuration illustrated in FIG. 2, in which the metal layers are provided on the inner surfaces of the dielectric material and the outer tubular layer, to a configuration in which the metal layers can be accessed from the outside of those layers.

Alternatively, a ceramic collar having a metal coating on the inside can be connected to the end of the inner tubular layer, so that the electrical connection to the inner metal layer can be picked up from the inside of the ceramic collar. Furthermore, an outer sheath having an internal metal coating at the electrosurgical instrument connection end and a metal ring at that end can be positioned over the outer metal layer, and the electrical connection to the outer metal layer can be picked up from the inside of the metal ring.

In one embodiment, an electrical signal from an inner metal layer coated on the outside of an inner tubular layer can be transferred to a metal ring to be used as a sliding electrical connection. This can be achieved by positioning a distal end of the inner tubular layer so that it is set back from a distal end of the dielectric layer (on an outer surface of which is coated the outer metal layer). A portion of the inside of the dielectric layer that extends from a proximal side of the distal end of the inner tubular layer to a distal side of the distal end of the inner tubular layer can be coated in conductive material. Thus, the electrical signal from the inner metal layer is transferred to the portion on the inside of the dielectric layer, because this portion is in contact with the inner metal layer. A metal ring (or tube) can be slid into the distal end of the dielectric layer so that it is adjacent to the distal end of the inner tubular layer. Since the metal ring is in contact with the portion on the inside of the dielectric layer that is coated in conductive material, the metal ring is electrically connected to the inner metal layer even when the metal ring is slidably displaced away from the inner tubular layer (provided that at least a part of the metal ring remains in contact with the portion on the inside of the dielectric layer). Thus, the metal ring comprises a sliding electrical connection to the inner metal layer, which may allow an electrosurgical instrument that is connected (directly or indirectly) to the metal ring to be slid axially relative to the inner metal layer while still remaining in electrical contact with the inner metal layer.

The invention claimed is:

1. A cable for conveying radiofrequency and/or microwave frequency energy to an electrosurgical instrument at a first end of the cable, the cable comprising:
   a hollow tube comprising inner and outer electrically conductive layers separated by dielectric material to form a transmission line;
   a first terminal at the first end of the cable for forming an electrical connection to the inner conductive layer;
   a second terminal at the first end of the cable for forming an electrical connection to the outer conductive layer;
   a rotatable component at the first end of the cable, wherein the rotatable component comprises a longitudinal passageway continuous with the hollow tube, and wherein the rotatable component is rotatable relative to the transmission line and comprises:
      a first portion electrically connected to the first terminal, wherein the first portion and the first terminal are rotatable relative to each other and are configured to maintain an electrical connection when rotated relative to each other; and
      a second portion electrically connected to the second terminal, wherein the second portion and the second terminal are rotatable relative to each other and are configured to maintain an electrical connection when rotated relative to each other,
   wherein the first portion and the second portion include the longitudinal passageway.

2. The cable according to claim 1, wherein the first terminal comprises a surface of an exposed part of the inner conductive layer.

3. The cable according to claim 2, wherein the exposed part of the inner conductive layer comprises an exposed tubular part of the inner conductive layer.

4. The cable according to claim 1, wherein:
   the first terminal is on an outer circumferential surface of the cable; and
   the first portion is positioned around the outer circumferential surface of the cable.

5. The cable according to claim 1, wherein:
   the first terminal is on an inner circumferential surface of the cable; and
   the first portion is positioned inside the inner circumferential surface of the cable.

6. The cable according to claim 1, wherein the first portion comprises conductive material on an inner surface or an outer surface thereof, the conductive material being in contact with the first terminal.

7. The cable according to claim 6, wherein the conductive material comprises a circumferential band of conductive material.

8. The cable according to claim 1, wherein the first portion comprises a conductive element biased into contact with the first terminal.

9. The cable according to claim 8, wherein the conductive element comprises a sprung wing, a sprung flap, a sprung pad or a sprung protrusion.

10. The cable according to claim 1, wherein the first portion comprises a hollow tube.

11. The cable according to claim 1 in which the first terminal is on an outer circumferential surface of the cable, and the first portion is positioned around the outer circumferential surface of the cable, wherein:
   the first portion comprises first and second sprung wings gripping the outer circumferential surface of the cable there-between.

12. The cable according to claim 1, in which the first terminal is on an inner circumferential surface of the cable, and the first portion is positioned inside the inner circumferential surface of the cable, wherein:
   the first portion comprises first and second sprung wings pressing outwards against the inner circumferential surface of the cable.

13. The cable according to claim 11, wherein the first portion comprises a hollow tube of naturally sprung material from which an axial strip has been removed from the circumference thereof to form the first and second sprung wings.

14. The cable according to claim 1, wherein the second terminal comprises a surface of an exposed part of the outer conductive layer.

15. The cable according to claim 14, wherein the exposed part of the outer conductive layer comprises an exposed tubular part of the outer conductive layer.

16. The cable according to claim 1, wherein:
   the second terminal is on an outer circumferential surface of the cable; and
   the second portion is positioned around the outer circumferential surface of the cable.

17. The cable according to claim 1, wherein:
   the second terminal is on an inner circumferential surface of the cable; and
   the second portion is positioned inside the inner circumferential surface of the cable.

18. The cable according to claim 1, wherein the second portion comprises conductive material on an inner surface or an outer surface thereof, the conductive material being in contact with the second terminal.

19. The cable according to claim 18, wherein the conductive material comprises a circumferential band of conductive material.

20. The cable according to claim 1, wherein the second portion comprises a conductive element biased into contact with the second terminal.

21. The cable according to claim 20, wherein the conductive element comprises a sprung wing, a sprung flap, a sprung pad or a sprung protrusion.

22. The cable according to claim 1, wherein the second portion comprises a hollow tube.

23. The cable according to claim 1, in which the second terminal is on an outer circumferential surface of the cable, and the second portion is positioned around the outer circumferential surface of the cable, wherein:

the second portion comprises first and second sprung wings gripping the outer circumferential surface of the cable there-between.

24. The cable according to claim 1, in which the second terminal is on an inner circumferential surface of the cable, and the second portion is positioned inside the inner circumferential surface of the cable, wherein:
the second portion comprises first and second sprung wings pressing outwards against the inner circumferential surface of the cable.

25. The cable according to claim 23, wherein the second portion comprises a hollow tube of naturally sprung material from which an axial strip has been removed from the circumference thereof to form the first and second sprung wings.

26. The cable according to claim 1, wherein the first portion is connected to, or integral with, the second portion.

27. A cable for conveying radiofrequency and/or microwave frequency energy to an electrosurgical instrument, the cable comprising:
a first part comprising an outer conductive layer provided on an outer side of a hollow tube of dielectric material;
a second part comprising an inner conductive layer;
wherein the second part is positioned inside the first part so that the inner conductive layer and the outer conductive layer form a transmission line;
wherein the second part is rotatable relative to the first part;
wherein the second part comprises a further conductive layer that is electrically connected to the outer conductive layer in a region where the outer conductive layer is exposed, the further conductive layer being electrically isolated from the inner conductive layer, wherein the further conductive layer and the outer conductive layer are rotatable relative to each other and are configured to maintain an electrical connection when rotated relative to each other; and
wherein the first part and the second part include a longitudinal passageway.

28. The cable according to claim 1, wherein the cable comprises actuating means fed through the hollow tube of the cable for rotating the rotatable component relative to the transmission line.

29. The cable according to claim 27, wherein the cable comprises actuating means fed through the hollow tube of the cable for rotating the second part relative to the first part.

30. The cable according to claim 28, wherein the actuating means is configured to be moved axially along the hollow tube of the cable, and wherein the cable comprises an interface provided in the hollow tube of the cable for converting axial movement of the actuating means into rotational movement of the rotatable component.

31. The cable according to claim 29, wherein the actuating means is configured to be moved axially along the hollow tube of the cable, and wherein the cable comprises an interface provided in the hollow tube of the cable for converting axial movement of the actuating means into rotational movement of the second part.

32. The cable according to claim 28, wherein the actuating means comprises an actuator element, and wherein the actuator element comprises a rod, wire, cable or hollow tube.

33. The cable according to claim 28, wherein:
the actuator element has a helical path provided on an outer surface thereof; and
the cable comprises a rotator having a follower that follows the helical path when the actuator element is moved axially, thereby causing the rotator to rotate.

34. The cable according to claim 28, wherein:
the actuator element comprises a follower on an outer surface thereof; and
the cable comprises a rotator having a helical path provided on an inner surface thereof along which the follower travels when the actuator element is moved axially, thereby causing the rotator to rotate.

35. The cable according to claim 33, wherein the helical path comprises a raised helical path.

36. The cable according to claim 33, wherein the helical path comprises a helical channel, a helical groove, or a helical slot.

37. The cable according to claim 33, wherein the follower comprises:
a protrusion;
a pin;
a fin;
a recess;
a groove;
a channel; or
a slot.

38. The cable according to claim 33, wherein the rotator is connected to, or is integral with, the electrosurgical instrument, so that rotation of the rotator causes rotation of the electrosurgical instrument.

39. The cable according to claim 33, in which the cable comprises the rotatable component, wherein the rotator is connected to, or is integral with, the rotatable component, so that rotation of the rotator causes rotation of the rotatable component.

40. The cable according to claim 1, wherein the dielectric material comprises:
a solid tube of dielectric material; or a tube of dielectric material having a porous structure.

41. The cable according to claim 1, wherein the inner conductive layer and/or the outer conductive layer comprises:
a conductive coating on the inside or outside of a tube of material;
a solid tube of conductive material positioned against the inside or outside of a tube of material; or
a layer of braided conductive material formed on, or embedded in, a tube of material.

42. The cable according to claim 1, wherein the cable comprises:
a hollow inner tubular layer;
a tube of the inner conductive layer on an outer surface of the hollow inner tubular layer;
a tube of the dielectric material on an outer surface of the tube of the inner conductive layer; and
a tube of the outer conductive layer on an outer surface of the tube of the dielectric material.

43. The cable according to claim 42, wherein the inner conductive layer protrudes beyond an edge of the tube of dielectric material, so that the inner conductive layer is exposed at the first end of the cable.

44. The cable according claim 1, wherein the cable comprises:
a hollow tube of the inner conductive layer;
a tube of the dielectric material on an outer surface of the hollow tube of the inner conductive layer; and
a tube of the outer conductive layer on an outer surface of the tube of the dielectric material.

45. The cable according to claim 44, wherein the cable further comprises a protective outer tubular layer on an outer surface of the tube of the outer conductive layer.

46. The cable according to claim 44, wherein the outer conductive layer protrudes beyond an edge of the tube of dielectric material, so that the outer conductive layer is exposed at the first end of the cable.

47. The cable according to claim 1, wherein an outer diameter of the cable is smaller over a portion of its length adjacent to the first end of the cable.

48. The cable according to claim 47, wherein the outer diameter of the cable is made smaller over the portion by reducing an internal diameter of the cable.

49. The cable according to claim 47, wherein the outer diameter of the cable is made smaller over the portion by reducing a thickness of the dielectric material.

* * * * *